United States Patent
Mansi et al.

(10) Patent No.: US 10,311,978 B2
(45) Date of Patent: Jun. 4, 2019

(54) METHOD AND SYSTEM FOR PATIENT SPECIFIC PLANNING OF CARDIAC THERAPIES ON PREOPERATIVE CLINICAL DATA AND MEDICAL IMAGES

(71) Applicants: Tommaso Mansi, Westfield, NJ (US); Bogdan Georgescu, Plainsboro, NJ (US); Xudong Zheng, Plainsboro, NJ (US); Ali Kamen, Skillman, NJ (US); Dorin Comaniciu, Princeton Junction, NJ (US)

(72) Inventors: Tommaso Mansi, Westfield, NJ (US); Bogdan Georgescu, Plainsboro, NJ (US); Xudong Zheng, Plainsboro, NJ (US); Ali Kamen, Skillman, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 1635 days.

(21) Appl. No.: 13/754,174

(22) Filed: Jan. 30, 2013

(65) Prior Publication Data
US 2013/0197881 A1  Aug. 1, 2013

Related U.S. Application Data

(60) Provisional application No. 61/592,113, filed on Jan. 30, 2012, provisional application No. 61/651,052, (Continued)

(51) Int. Cl.
G06F 17/50 (2006.01)
A61B 5/055 (2006.01)
(Continued)

(52) U.S. Cl.
CPC ......... G16H 50/50 (2018.01); A61B 5/0044 (2013.01); A61N 1/3627 (2013.01);
(Continued)

(58) Field of Classification Search
CPC ............. G06F 17/5009; G06F 17/5018; G06F 2217/16
(Continued)

(56) References Cited

U.S. PATENT DOCUMENTS 5,947,899 A * 9/1999 Winslow .................. A61B 5/00
                                                    600/410
6,317,631 B1 * 11/2001 Ben-Haim ........... A61B 5/0215
                                                    607/2
(Continued)

OTHER PUBLICATIONS

Comas et al. "A Shell Model for Reat-Time Simulation of Intra-ocular Implant Deployment", Biomedical Simulation Lecture Notes in Computer Science vol. 5958, 2010, pp. 160-170, Springer-Verlag Berlin Heidelberg 2010.*
(Continued)

*Primary Examiner* — Kamini S Shah
*Assistant Examiner* — Iftekhar A Khan

(57) ABSTRACT

A method and system for patient-specific planning of cardiac therapy, such as cardiac resynchronization therapy (CRT), based on preoperative clinical data and medical images, such as ECG data, magnetic resonance imaging (MRI) data, and ultrasound data, is disclosed. A patient-specific anatomical model of the left and right ventricles is generated from medical image data of a patient. A patient-specific computational heart model, which comprises cardiac electrophysiology, biomechanics and hemodynamics, is generated based on the patient-specific anatomical model of the left and right ventricles and clinical data. Simulations of cardiac therapies, such as CRT at one or more anatomical locations are performed using the patient-specific computational heart (Continued)

model. Changes in clinical cardiac parameters are then computed from the patient-specific model, constituting predictors of therapy outcome useful for therapy planning and optimization.

24 Claims, 18 Drawing Sheets

Related U.S. Application Data filed on May 24, 2012, provisional application No. 61/704,726, filed on Sep. 24, 2012.

(51) Int. Cl.
| | | |
|---|---|---|
| *A61N 1/362* | (2006.01) | |
| *A61N 1/365* | (2006.01) | |
| *G06F 19/00* | (2018.01) | |
| *G06T 17/00* | (2006.01) | |
| *G09B 23/30* | (2006.01) | |
| *G16H 50/50* | (2018.01) | |
| *A61B 5/00* | (2006.01) | |
| *A61B 8/08* | (2006.01) | |

(52) U.S. Cl.
CPC ..... *A61N 1/36514* (2013.01); *A61N 1/36585* (2013.01); *G06F 19/00* (2013.01); *G06T 17/00* (2013.01); *G09B 23/30* (2013.01); *A61B 5/055* (2013.01); *A61B 8/0883* (2013.01); *A61B 2576/023* (2013.01); *G06T 2210/41* (2013.01)

(58) Field of Classification Search
USPC .......................................................... 703/2
See application file for complete search history.

(56) References Cited

U.S. PATENT DOCUMENTS

| | | | |
|---|---|---|---|
| 7,828,735 B2* | 11/2010 | Holmes ................. | A61B 5/055 600/450 |
| 8,098,918 B2 | 1/2012 | Zheng et al. | |
| 8,386,188 B2 | 2/2013 | Taylor et al. | |
| 9,603,539 B2* | 3/2017 | Xue .................... | A61B 5/04012 |
| 2003/0109785 A1* | 6/2003 | Buck ........................ | A61B 8/06 600/437 |
| 2006/0099194 A1* | 5/2006 | Geng .................. | A01K 67/0275 424/93.21 |
| 2007/0270703 A1* | 11/2007 | He ....................... | A61B 5/0422 600/509 |
| 2008/0065061 A1* | 3/2008 | Viswanathan ......... | A61B 5/042 606/41 |
| 2008/0262814 A1* | 10/2008 | Zheng ................. | G06F 19/3437 703/11 |
| 2008/0319308 A1* | 12/2008 | Tang ...................... | A61B 5/055 600/416 |
| 2010/0070249 A1* | 3/2010 | Ionasec ................. | G06F 19/321 703/2 |
| 2010/0280352 A1* | 11/2010 | Ionasec ................. | A61B 5/0263 600/407 |
| 2011/0060576 A1* | 3/2011 | Sharma ................. | G06T 7/0012 703/11 |
| 2011/0092809 A1* | 4/2011 | Nguyen ................. | A61B 5/042 600/424 |
| 2012/0022843 A1 | 1/2012 | Ionasec et al. | |
| 2012/0030255 A1* | 2/2012 | Xue .................... | A61B 5/04012 707/805 |
| 2012/0041301 A1 | 2/2012 | Redel | |
| 2012/0072190 A1 | 3/2012 | Sharma et al. | |
| 2012/0121151 A1 | 5/2012 | Bernhardt et al. | |
| 2012/0203530 A1 | 8/2012 | Sharma et al. | |
| 2012/0284003 A1* | 11/2012 | Gosh .................... | A61B 5/0402 703/2 |
| 2013/0066618 A1* | 3/2013 | Taylor ................ | A61B 5/02007 703/11 |
| 2013/0072790 A1* | 3/2013 | Ludwig .................... | A61B 6/52 600/425 |
| 2013/0226542 A1* | 8/2013 | Rapaka ................ | G06K 9/6207 703/2 |
| 2013/0310890 A1* | 11/2013 | Sweeney ............ | A61B 5/04028 607/25 |
| 2014/0088943 A1* | 3/2014 | Trayanova ......... | A61B 5/04021 703/11 |
| 2014/0122048 A1* | 5/2014 | Vadakkumpadan ........................ A61B 5/7275 703/11 |
| 2015/0294082 A1* | 10/2015 | Passerini ................ | G16H 50/50 703/11 |

OTHER PUBLICATIONS

Dikici et al., "Quantification of Delayed Enhancement MR Images", In Proc. MICCAI 2004, LNCS 3216, pp. 250-257, 2004.

Peyrat et al., "A Computational Framework for the Statistical Analysis of Cardiac Diffusion Tensors: Application to Small Database of Canine Hearts", IEEE TMI, 26(11): 1500-1514, 2007.

Mitchell et al., "A Two-Current Model for the Dynamics of Cardiac Membrane", Bulletin of Mathematical Biology, 65(5):767-793, 2003.

Powell, "Developments of NEWUOA for Minimization Without Derivatives", J. Num. Analysis, 2008.

\* cited by examiner

| ALGORITHM 1: HEART MODEL PERSONALIZATION |
|---|
| 1. PERSONALIZE THE WINDKESSEL PARAMETERS FOR AORTA AND PULMONARY ARTERY USING MEASURED VOLUME AND PRESSURE CURVES. AN EXHAUSTIVE SEARCH APPROACH IS EMPLOYED. |
| 2. RUN THE SIMULATION WITH ADJUSTED WINDKESSEL PARAMETERS AND DEFAULT ELECTROMECHANICAL PARAMETERS. |
| 3. SYNCHRONIZE THE SIMULATION WITH THE MEASURED VOLUME CURVE:<br>   a. ADJUST EP STIMULUS TIME $T_{init}$ TO MATCH ATRIAL CONTRACTION TIME WITH MEASURED VOLUME CURVE.<br>   b. ADJUST GLOBAL APD DURATION TO MATCH SYSTOLE DURATION MEASURED IN THE VOLUME CURVE |
| 4. MATCH THE SIMULATED EJECTION FRACTION AND WAVE FORM OF VENTRICULAR VOLUME WITH MEASUREMENTS BY ADJUSTING $\sigma_0$, $K_{ATP}$ AND $K_{RS}$ |
| 5. MATCH THE LV PRESSURE MEASUREMENT BY ADJUSTING $\sigma_0$ AND E (YOUNG'S MODULUS) AS WELL AS THE PULMONARY VEIN PRESSURE TO SHIFT THE LEFT ATRIUM BASELINE PRESSURE TOWARDS MEASUREMENTS. |

FIG. 16

METHOD AND SYSTEM FOR PATIENT SPECIFIC PLANNING OF CARDIAC THERAPIES ON PREOPERATIVE CLINICAL DATA AND MEDICAL IMAGES

This application claims the benefit of U.S. Provisional Application No. 61/592,113, filed Jan. 30, 2012, and U.S. Provisional Application No. 61/704,726, filed Sep. 24, 2012, the disclosures of which are herein incorporated by reference.

BACKGROUND OF THE INVENTION

The present invention relates to patient-specific simulations for planning cardiac resynchronization therapy, and more particularly, to simulations using multi-scale computational models of heart ventricles personalized from preoperative clinical data and medical images to predict outcomes of cardiac resynchronization therapy for a patient.

Patients with heart failure often present dysynchronous ventricular contraction. For example, the left ventricle (LV) and right ventricle (RV) do not beat synchronously, which decreases the efficiency of the cardiac pump. Cardiac Resynchronization Therapy (CRT) treats this condition by artificially pacing the cardiac muscle through an advanced pacemaker with several pacing leads. In order to implement CRT in a patient, a pulse generator (pacemaker) and multiple leads, including a left ventricle lead, a right ventricle lead, and a right atrial lead, are used to synchronize ventricle contraction in a patient. Although CRT is typically an efficient treatment of heart failure, thirty percent of patients do not respond to the therapy even though they are within the recommended guidelines for CRT. In such cases, the patient's heart does not improve as a result of the CRT and the ejection fraction, which is a measure of cardiac efficiency, stays constant despite the therapy.

BRIEF SUMMARY OF THE INVENTION

The present inventors have determined that a predictive framework is desirable to select patients that will respond to Cardiac Resynchronization Therapy (CRT), and to optimize lead placement and programming to increase the number of suitable patients. The present invention provides a method and system for patient-specific CRT planning based on preoperative medical image data, such as magnetic resonance imaging (MRI) or Ultrasound data. Embodiments of the present invention provide an integrated system based on multi-scale computational models of heart ventricles personalized from preoperative patient data and medical image data to provide metrics that quantify the acute outcomes of CRT in a patient, such as heart dynamics, ventricular volume, cardiac synchrony, and pressure curves.

In one embodiment of the present invention, a patient-specific anatomical model of left and right ventricles is generated from medical image data of a patient. A patient-specific computational heart model is generated based on the patient-specific anatomical model of the left and right ventricles. CRT is simulated at one or more anatomical locations using the patient-specific computational heart model.

These and other advantages of the invention will be apparent to those of ordinary skill in the art by reference to the following detailed description and the accompanying drawings.

BRIEF DESCRIPTION OF THE DRAWINGS

FIG. 16 illustrates an algorithm for determining patient-specific parameters of the computational heart model according to an embodiment of the present invention;

DETAILED DESCRIPTION

The present invention relates to patient-specific Cardiac therapy planning based on preoperative clinical data and medical images, such as ECG, MRI and/or Ultrasound data. In an advantageous embodiment, the present invention is illustrated on the specific case of cardiac resynchronization therapy (CRT). Embodiments of the present invention are described herein to give a visual understanding of the patient-specific CRT simulation methods. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
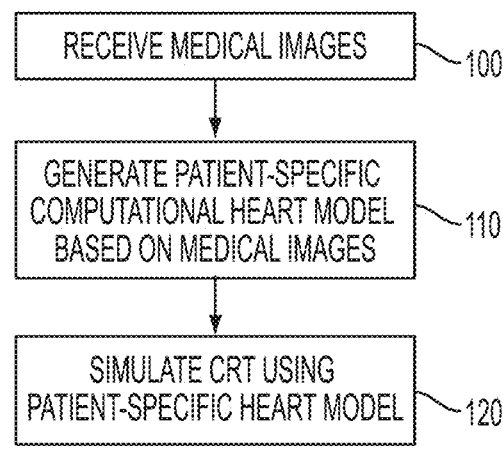
FIG. 1 illustrates a method for patient-specific CRT planning according to an embodiment of the present invention.

FIG. 1 illustrates a method for patient-specific CRT planning according to an embodiment of the present invention. As illustrated in FIG. 1, at step 100 clinical data and medical images of a patient are received. The clinical data can include electrophysiology data such as ECG and/or pressure data such as invasive catheter measurements or pressure cuff measurements. The medical images can be 3D preoperative images of the patient. The medical images may be a sequence of medical images acquired over at least one complete heart cycle. In advantageous embodiments of the present invention, the medical images can be MRI images and/or ultrasound images, but the present invention is not necessarily limited to these imaging modalities. The medical images may be received directly from a medical imaging device, such as an MR or ultrasound scanner, or the medical images may be received by loading stored medical images of a patient. At step 110, a patient-specific computational heart model is generated based on the medical images. At step 120, CRT is simulated using the patient-specific computational heart model.

Figure 2:
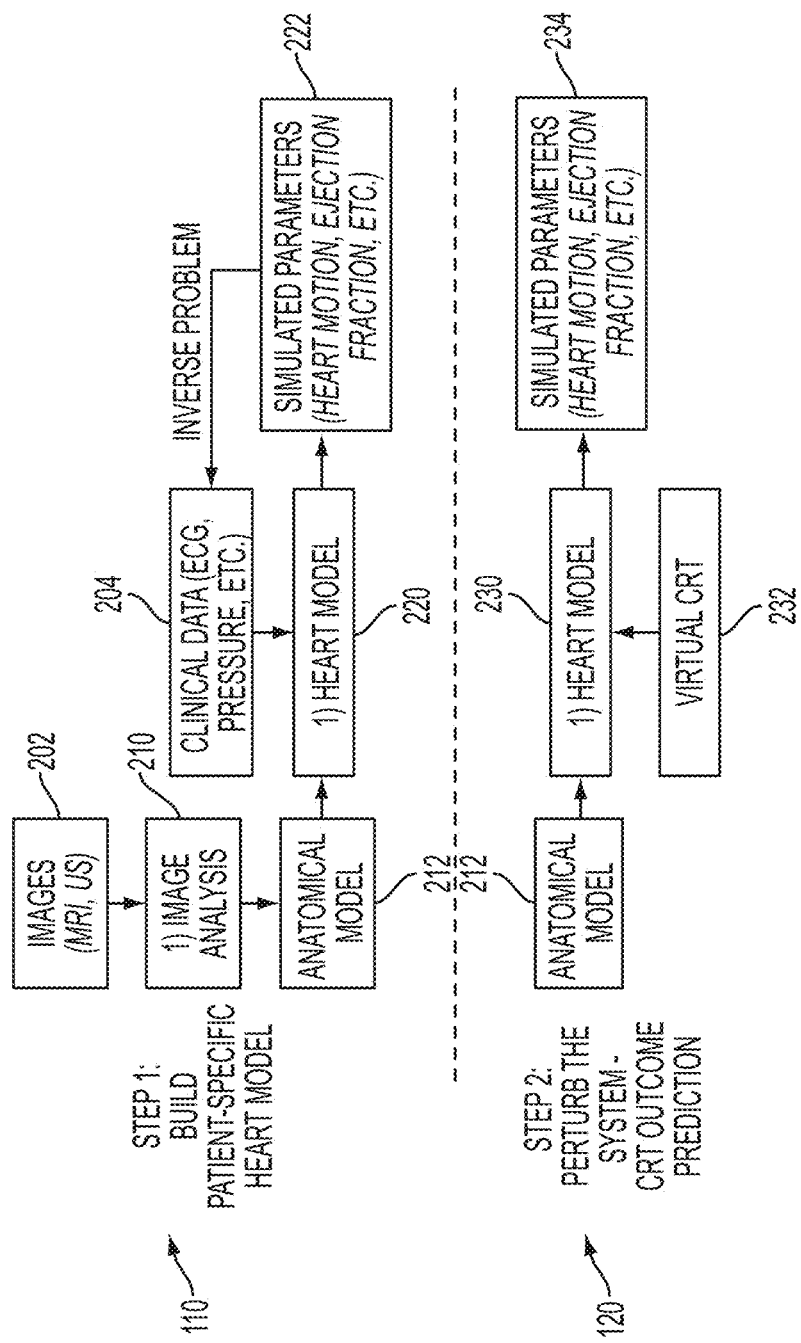
FIG. 2 illustrates an overview of a framework for implementing the method of FIG. 1 according to an embodiment of the present invention.

FIG. 2 illustrates an overview of a framework for implementing the method of FIG. 1 according to an embodiment of the present invention. As illustrated in FIG. 2, in a first stage corresponding to step 110 of FIG. 1, the patient-specific computational heart model is built, and in a second stage corresponding to step 120 of FIG. 1, CRT outcomes are predicted by perturbing the computational heart model to simulate CRT. In the first stage (110), medical images 202, such as MRI and Ultrasound images, and patient-specific clinical data 204, such as ECG, pressure measurements, etc., are received as inputs. At step 210, an automated image analysis is performed to generate a patient-specific anatomical model 212 of the ventricles. At step 220, a patient-specific computational heart model is generated based on the personalized anatomic model 212 calculated from the images 202 and the clinical data 204. In particular, the patient-specific computational heart model is generated using an inverse problem to adjust parameters of the computational heart model such that simulated parameters 222, such as heart motion, ejection fraction, etc., output by the patient-specific computational heart model match the clinical data 204 observed for the patient. At the end of this stage, the model is completely generative and the heart function of the patient is accurately reproduced in the computer system performing the method.

In the second stage (120), virtual CRT 232 is applied to represent pacing of the computational heart model at various anatomical locations. At step 230, simulations are performed by perturbing the patient-specific computational heart model based on the virtual CRT 232 at different anatomical locations. The simulations evolve according to the biophysical laws represented by the model parameters calculated at step 220. Simulated parameters 234, such as ejection fraction, ECG, and heart dynamics, are calculated based on the CRT simulations, and such simulated parameters 234 are used as predictors of the patient response to CRT.

Figure 3:
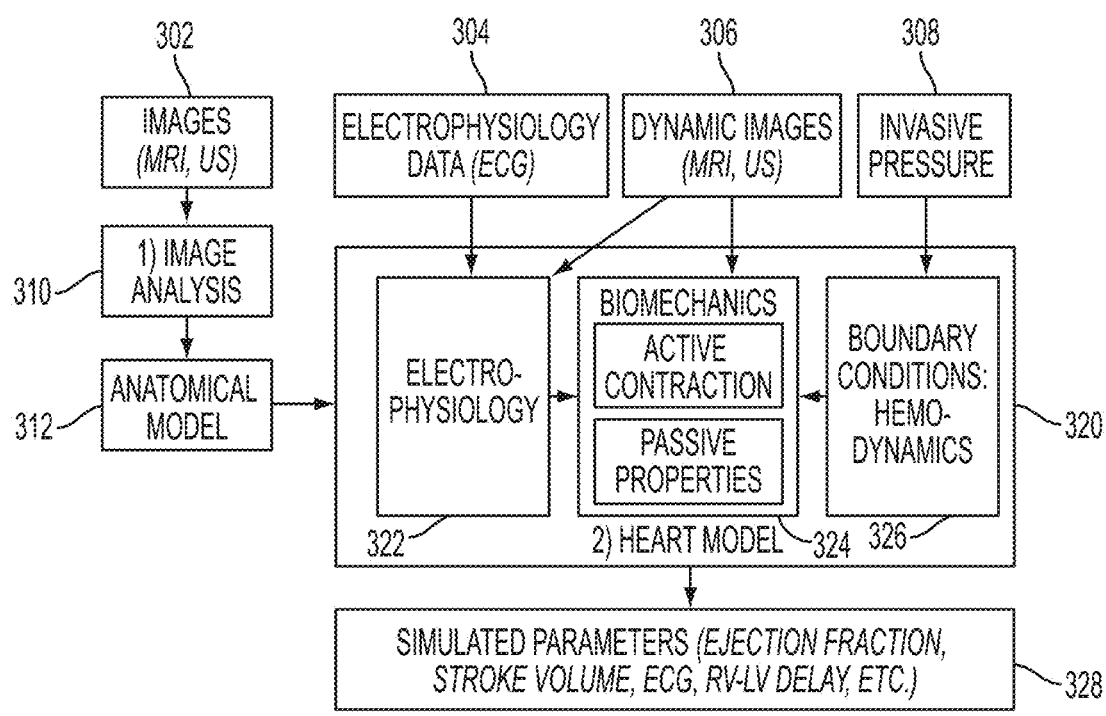
FIG. 3 illustrates a detailed framework of the computational heart model component to describe the multi-physics interactions considered in the computational heart model according to an embodiment of the present invention.

FIG. 3 illustrates a detailed framework of the computational heart model component to describe the multi-physics interactions considered in the computational heart model according to an embodiment of the present invention. As illustrated in FIG. 3, the patient-specific heart model includes four main modules representing cardiac anatomy, cardiac electrophysiology, cardiac biomechanics, and cardiac boundary conditions. These modules are connected as follows. Starting from a medical image 302 of the heart (MRI, Ultrasound), at step 310, a detailed anatomical model 312 of the patient's heart is generated. In an exemplary embodiment, a detailed anatomical model is generated of the two ventricles only, as CRT targets ventricular dysynchrony. Arteries and atria are modeled as boundary conditions of the system. The anatomical model 312 comprises the bi-ventricular geometry, the orientation of myocyte fibers, and any information that varies spatially such as action potential duration, scars, etc. The anatomical model 312 is then given as input to the Heart Model subsystem (step 320), which will compute myocardium motion over time according to three main sub-parts: cardiac electrophysiology 322, tissue biomechanics 324, and boundary conditions 326. Each of these sub-parts are adjusted to patient data using inverse problem approaches and all available preoperative data such as dynamic images 306, ECG 304, invasive pressure measurements 308, etc, such that the simulated parameters 330 match the clinical observations. Once the model is personalized, CRT is simulated by pacing the model at various locations. Clinical parameters are computed from the simulation to quantify the predicted patient response to the therapy.

Figure 4:
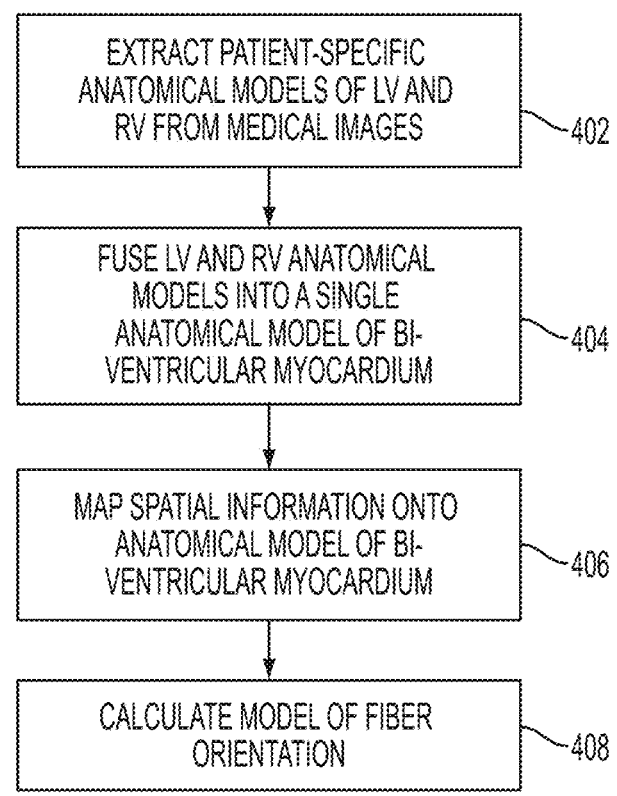
FIG. 4 illustrates a method for generating the patient-specific anatomical model according to an embodiment of the present invention.

FIG. 4 illustrates a method for generating the patient-specific anatomical model according to an embodiment of the present invention. The method of FIG. 4 can be used to implement the image processing step 310 shown in FIG. 3 in order to generate the anatomical model 312. At step 402, anatomical models of the LV and RV are extracted from the medical images. In an advantageous embodiment, the LV and RV anatomical models show patient-specific heart morphology and dynamics, and are calculated automatically from MRI or ultrasound images. Although it is possible to extract models for all of the heart chambers, in an advantageous embodiment, only the geometry LV and RV are explicitly modeled.

In particular, for each of the LV and the RV, the heart chamber segmentation can be formulated as a two-step learning problem: anatomical structure localization and boundary delineation. In an advantageous embodiment, marginal space learning (MSL) can be used to apply machine learning to 3D object detection. The idea of MSL is not to learn a monolithic classifier directly in the full similarity transformation parameter space but to incrementally learn classifiers on marginal spaces. In particular, the detection of each heart chamber can be split into three problems: position estimation, position-orientation estimation, and position-orientation-scale estimation. A separate classifier is trained based on annotated training data for each of these estimation problems. The classifiers in the lower dimensional marginal spaces are used to prune the searching space efficiently. This object localization stage results in an estimated transformation (position, orientation, and scale) of the object (e.g., heart chamber).

After automatic object localization, the mean shape model of the object is aligned with the estimated transformation to get a rough estimate of the object shape. The shape is then deformed locally to fit the object boundary. Active shape models (ASM) can be used to deform an initial estimate of a non-rigid shape under the guidance of the image evidence and the shape prior. However, a non-learning based generic boundary detector, as used in conventional ASM applications, does not work effectively in heart chamber deformation due to the complex background and weak edges. Instead, a learning based boundary detector can be used to exploit more image evidences to achieve a robust boundary detection. Additional details regarding MSL-based heart chamber segmentation are described in U.S. Pat. No. 7,916,919, issued Mar. 29, 2011, and entitled "System and Method for Segmenting Chambers of a Heart in a Three Dimensional Image", United States Published Patent Application No. 2010/0040272, and United States Published Patent Application No. 2012/0022843, which are incorporated herein by reference.

Figure 5:
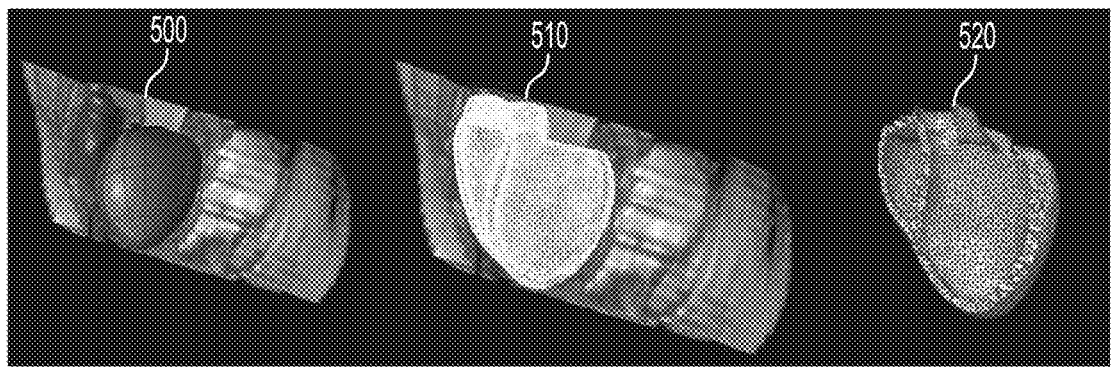
FIG. 5 illustrates fusion of LV and RV surface models.

At step 404, the patient-specific LV and RV models are fused into a single anatomical model of the bi-ventricular myocardium. In particular, the LV and RV anatomies extracted in step 402 are fused into a single volumetric mesh representation. The LV and RV models can be fused into a single volumetric mesh representation using the Computational Geometry Algorithms Library (CGAL), on which vertices are tagged into surface zones according to the underlying anatomy. According to an advantageous embodiment, tetrahedral elements can be used to accurately represent the details of the bi-ventricular anatomy. FIG. 5 illustrates fusion of LV and RV surface models. As shown in FIG. 5, image 500 shows surface models detected for the LV endocardium, LV epicardium, and RV. Image 510 shows a bi-ventricular anatomical model 512 resulting from fusing the LV and RV surface models by tagging vertices into surface zones according to the underlying anatomy. Image 520 shows a volumetric tetrahedral mesh of the anatomical model of the bi-ventricular myocardium.

Returning to FIG. 4, at step 406, spatial information is mapped onto the anatomical model of the bi-ventricular myocardium. Spatial information, such as scars, grey zones, and fibrosis can be identified in images, such as late enhancement MRI. For example, the spatial information may be automatically identified using trained classifiers or may be manually identified by clinician. The spatial information is mapped onto the tetrahedral mesh representing the bi-ventricular myocardium. This information is important to simulate the electrical wave around scars, in particular for wave-reentry assessment and correctly capture impaired cardiac mechanics due to ill-functioning or dead cells.

Figure 6:
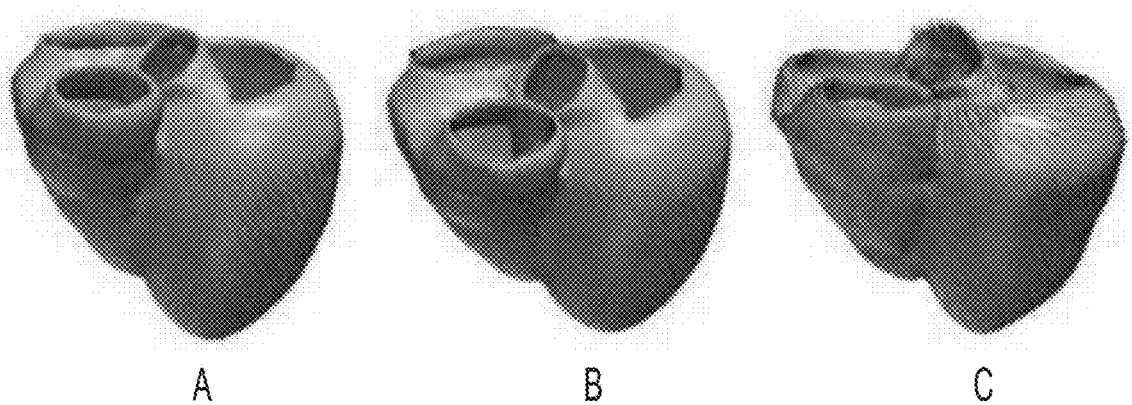
FIG. 6 illustrates exemplary results for calculating a computational model of fiber orientation.

At step 408, model of fiber orientation is automatically calculated based on the patient-specific geometry. In an advantageous embodiment, the model of fiber orientation can be automatically calculated using a rule-based approach. The elevation angle of the fibers, i.e., their angle with respect to the short axis plane, varies almost linearly from +70° on the epicardium to 0° at mid-wall to +70° on the endocardium. From the LV apex to the LV base, endocardial and epicardial fibers have a constant elevation angle. From the base plane to the valves, special care is taken in order to achieve smooth and realistic fiber variations. The fiber orientations around the valves are specified as: circumferential around the mitral, tricuspid, and pulmonary valves, and longitudinal around the left ventricle outflow tract. A geodesic interpolation of the fibers on the endocardium and epicardium is then performed between the base plane and the valves. Fibers across the myocardium are then calculated by linear interpolation. Because fibers can vary from patient to patient, the user can manually set the elevation angles regionally on the mesh. FIG. 6 illustrates exemplary results for calculating a computational model of fiber orientation. As shown in image A of FIG. 6, fibers below the base plane (between the base plane and the apex) are calculated first. As shown in image B, the fibers around the valves are then set. As shown in image C, the fibers throughout the myocardium are calculated by geodesic interpolation.

Returning to FIG. 3, once the patient-specific anatomical model 312 is generated using the method of FIG. 4, at step 320, the patient-specific computational heart model is generated by determining patient-specific parameters for the cardiac electrophysiology module 322, cardiac biomechanics module 324, and cardiac boundary conditions module 326, using the patient-specific anatomical model as input. The first biophysical phenomenon that needs to be simulated in the cardiac electrophysiology (322), as it commands the cardiac contraction. The cardiac electrophysiology is also important for CRT prediction. Numerous electrophysiological models have been proposed, dealing with different biological scales and theoretical complexity. These models can be organized into three different categories: biophysical, phenomenological and Eikonal.

Biophysical models simulate the ionic interactions across the cell membranes and the biological phenomena underlying ion channels. As a result, these models are very detailed and controlled by more than 50 parameters related to each ion interaction and cell function. The cell model is then integrated at the tissue scale using reaction-diffusion partial differential equations (PDE).

Phenomenological models were developed from experimental observations on nerves or myocardium tissues. Intuitively, these models reproduce the observed shape of the action potential and how it changes under external conditions, without focusing on the underlying ionic phenomena. Hence, they are simplifications of the above-mentioned biophysical models since they work at a more macroscopic level. They depend on much fewer parameters, typically 2 to 3, which are directly related to the action potential shape or ECG measurements, making their personalization from clinical data more feasible. Like the biophysical models, phenomenological models are integrated at the organ scale using reaction diffusion PDEs.

Eikonal models further simplify the mathematical formulation of cardiac electrophysiology by considering the sole propagation of the electrical wave. The action potential is not directly simulated but the propagation of the electrical wave, by computing the time it arrives at a given spatial location of the myocardium. These models are governed by only one or two parameters and they can be solved very efficiently using anisotropic Fast Marching Methods. Eikonal models are therefore suited for real-time simulations as one full-heart depolarization can be simulated in about 1 minute.

The model implemented in an advantageous embodiment of the present invention considers inflow and outflow currents across the cell membranes as two lumped variables. The current sent by the pacing leads of the CRT device can therefore be easily added to the model. Embodiments of the present invention rely on the mathematical model of action potential proposed by Mitchell et al., "A Two-Current Model for the Dynamics of Cardiac Membrane", *Bulletin of Mathematical Biology*, 65(5):767-793, 2003, which is incorporated herein by reference, since its parameters are directly related to the shape of the action potential. This model is referred to herein as the "Mitchell-Schaeffer" model or "M-S" model. A diffusion term is added into the original M-S model to mimic wave propagation throughout the patient-specific anatomical model. There are two unknowns in the model: the trans-membrane potential, or voltage v(t), and a gating variable h(t), which models the state of the ion channels (opening/closing). As expressed in Equation (1) below, the temporal change of the trans-membrane potential is equal to the summation of the inward current, outward current, stimulated current and diffusion term:

$$\frac{dv}{dt} = J_{in}(v, h) + J_{out}(v) + J_{stim}(t) + \nabla(K\nabla v). \quad (1)$$

$J_{in}$ is the inward current and is computed using Equation (2):

$$J_{in}(v, h) = \frac{hC(v)}{\tau_{in}}, \quad (2)$$

where the cubic function $C(v)=v^2(1-v)$ describes the voltage dependence of the inward current, which mimics the behavior of the fast acting gates, and $\tau_{in}$ is a time constant. $J_{out}$ is the outwards current and is computed using Equation (3). Since it is the outward current, it decreases the membrane and has a minus sign:

$$J_{out}(v) = -\frac{v}{\tau_{out}}. \qquad (3)$$

$J_{stim}$ is the stimulated current which is applied externally by the CRT leads. Parameters from manufacturers can be integrated directly into the model. For the diffusion term, K is the diffusivity and is anisotropic for tissue. The gating variable h(t) is a non-dimensional variable which varies between 0 and 1. When the gate is open, h=1. When the gate is closed, h=0. The evolution of h(t) is governed by the ODE below:

$$\frac{dh}{dt} = \begin{cases} \dfrac{1-h}{\tau_{open}} & v < v_{gate} \\ \dfrac{-h}{\tau_{close}} & v > v_{gate} \end{cases}, \qquad (4)$$

where $\tau_{open}$ and $\tau_{close}$ are the time constants with which the gate opens and closes, and $v_{gate}$ is the change-over voltage.

Figure 7:
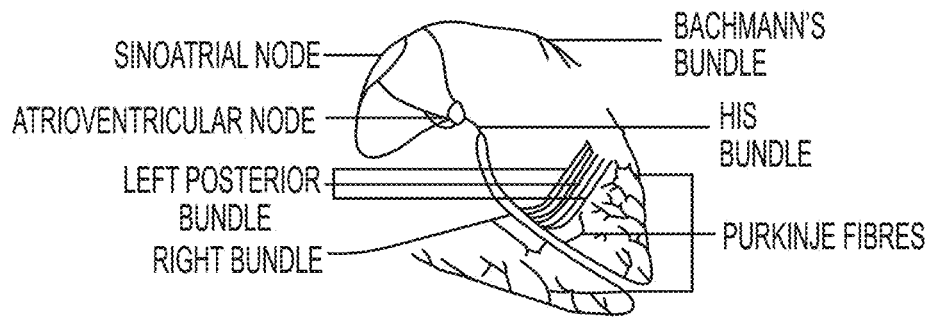
FIG. 7 illustrates the electrophysiological conduction system of the heart.

In an advantageous implementation, the model is extended to consider Purkinje fibers. FIG. 7 illustrates the electrophysiological conduction system of the heart. As shown in FIG. 7, the electrophysiological conduction system of the heart is composed of several elements including the sinoatrial node, atrioventricular node, His bundle, and Purkinje fibers. The electrical wave starts in the atria, at the sinoatrial node, the physiological pacemaker. As the electrical wave propagates towards the atrioventricular node, it depolarizes the atrial myocytes, which contract and pump blood to the ventricles. The electrical impulse is then stopped for a few milliseconds to synchronize the heart. This "pause" is fundamental as it enables the atria to fully contract and completely pump the blood into the ventricles. Finally, the electrical wave is propagated at a very high speed downwards to the apex (tip of the heart) through the left and right bundles branches. The electrical wave reaches the Purkinje fibers and propagates throughout the entire myocardium, from endocardium to epicardium, at a lower speed. Thus, in order to model the cardiac dynamics accurately, each component needs to be modeled properly.

In general, the anatomical structures of the Purkinje network cannot be extracted from medical imaging modalities. In order to mimic the fast propagation of electrical waves along the Purkinje fibers while keeping the problem tractable, embodiments of the present invention implement a "macro-scale" model of Purkinje fibers. For this model, it is assumed that the Purkinje fibers are evenly distributed on the entire endocardial surface. Thus, the Purkinje fibers can be modeled as a "continuous" membrane rather than a complex network. The above-described two-current Mitchell-Schaeffer equations can be solved on this membrane using two-dimensional finite element formulation. In order to take into account the complex three dimensional shape of the endocardial surface, the finite element formulation is first built on each local, planar coordinate and then is rotated back into the global coordinate system to perform the final assembly. The fast propagation is implemented by setting a high diffusion coefficient $K_{Purkin}$. The coupling between the "macro-scale" Purkinje fiber model and the myocardium is implemented through boundary conditions. Here, one way coupling is employed to link the Purkinje fiber with the myocardium. At each time step, the electrophysiological equation (Equation 1) is first solved on the endocardial triangulation defining the domain of the macro-scale Purkinje fiber. Since the endocardial triangulation has one-to-one mapping with the tetrahedral vertices at the endocardium, Dirichlet boundary conditions can be specified for the myocardium so that the potential at these tetrahedral nodes are set equal to the corresponding triangulation nodes. The equations are then solved on the entire myocardium.

Cardiac electrophysiology is calculated by integrating this PDE system over time, at every node of the patient-specific anatomical model. A semi-implicit first order time discretization scheme is used to ensure numerical stability. The reaction-diffusion model is solved on the patient mesh using finite elements. The model is initialized on the septal surface at a user-defined frequency that is adjusted from the ECG. When simulating CRT, CRT leads are modeled by adding $J_{stim}$ current at the mesh vertices were the lead is placed.

The cardiac electrophysiology model is personalized from the patient's ECG, dynamic images, and, if available, endocardial mappings. If only ECG is available, the simulated QRS (heartbeat) is aligned with measured QRS by adjusting tissue diffusivity (parameter K in Equation (1)). If endocardial mappings are available, inverse problem methods are used to estimate tissue conductivity and $\tau_{close}$ by comparing the simulated isochrones and potentials with measurements. Finally, dynamic images can be used to adjust electrophysiology overall synchrony by minimizing the difference of the cardiac motion computed from the electrophysiology model and the observations. Bundle branch blocks can be simulated by modifying the activation times of the left and right ventricles.

The second component of the computational heart model is the cardiac biomechanics module 324, which mimics cardiac biomechanics based on the electrophysiology simulated by the cardiac electrophysiology module 322. The biomechanics module 324 is therefore closely linked to the cardiac electrophysiology module 322. The myocardium is an active, non-linear, anisotropic visco-elastic tissue whose motion is controlled by the cardiac electrophysiology. Its constitutive law, which describes its elastic behavior, comprises an active component, the active contraction of the muscle controlled by the action potential, and a passive component, the elasticity of the tissue. They are linked together according to the Hill-Maxwell framework. In practice, the active contraction is viewed as a transient external force that makes the myocardium contract. The passive properties of the tissue are internal forces that ensure realistic motions. Models of myocardium passive properties aim to reproduce how the myocardium deforms under given stress (e.g., active contraction) and boundary conditions (e.g., endocardial pressure). Mathematically, they amount to solving the PDEs of the constitutive laws of myocardium tissue on the patient anatomical model.

A large variety of models have been proposed to simulate myocardium passive properties. The simplest approach consists in using transverse isotropic linear elasticity which assumes linear relationship between strain and stress. Linear elasticity is often implemented within the infinitesimal, linear strain theory for computational efficiency, which becomes inaccurate for large deformations. Methods to handle correctly the large deformations have been proposed. The Total Lagrangian Explicit Dynamics (TLED) algorithm is an efficient non-linear framework that can be implemented on graphics processing units (GPU). However, TLED may require very small time steps for numerical stability. Alternatively, co-rotational approaches have been proposed to improve the infinitesimal strain implementation. The idea is to compute the deformation in a local coordinate system that "rotates" with the elements.

However, heart tissue is non-linear. Constitutive laws have been derived by stretching slabs of myocardium tissues in several directions using biaxial machines to measure tissue strain under known load. Hyper-elastic laws have been therefore developed for more realistic simulations, like the pole-zero law or the more recent Costa law. That model considers not only fiber orientation, but also their organization in sheets across the myocardium. Yet, improving the model accuracy is achieved at the price of complexity, with increasing number of parameters. The Costa law for instance is governed by seven parameters, most of them difficult to estimate in-vivo.

In a first embodiment of the present invention, the passive properties of the myocardium are modeled using co-rotational elasticity. In this embodiment, the tissue passive properties are modeled using linear elasticity and Hooke's law. The elastic stress is directly related to the strain by the equation $\sigma = C:\varepsilon$, where $\sigma$ is the stress tensor, C is a $4^{th}$ order tensor of tissue constitutive law, and $\varepsilon$ is the strain tensor computed from the reference position of the patient's anatomy. For transverse isotropic material like the myocardium, the matrix C is built in the local coordinate system of the fiber orientation according to the following inverse relationship:

$$\begin{bmatrix} \epsilon_{xx} \\ \epsilon_{yy} \\ \epsilon_{zz} \\ 2\epsilon_{yz} \\ 2\epsilon_{zx} \\ 2\epsilon_{xy} \end{bmatrix} = \begin{bmatrix} \frac{1}{E_x} & -\frac{v_{yx}}{E_y} & -\frac{v_{yx}}{E_y} & 0 & 0 & 0 \\ -\frac{v_{xy}}{E_x} & \frac{1}{E_y} & -\frac{v_{yz}}{E_y} & 0 & 0 & 0 \\ -\frac{v_{xy}}{E_x} & -\frac{v_{yz}}{E_y} & \frac{1}{E_y} & 0 & 0 & 0 \\ 0 & 0 & 0 & \frac{2(1+v_{yz})}{E_y} & 0 & 0 \\ 0 & 0 & 0 & 0 & \frac{1}{G_{xy}} & 0 \\ 0 & 0 & 0 & 0 & 0 & \frac{1}{G_{xy}} \end{bmatrix} \begin{bmatrix} \sigma_{xx} \\ \sigma_{yy} \\ \sigma_{zz} \\ \sigma_{yz} \\ \sigma_{xx} \\ \sigma_{xy} \end{bmatrix} \quad (5)$$

$E_x$, $E_y$, $E_z$ are the Young's moduli in each direction (X is along the fiber direction, Y and Z are defined accordingly), $v_{ij}$ are the Poisson ratios for each direction, and $G_{xy}$ is the shear modulus. Co-rotational linear tetrahedra are used to cope with the large deformations and rotations observed in heart motion, in particular during systole.

In a second embodiment of the present invention, a non-linear model is used to model the passive properties of the myocardium tissue. The present inventors recognized the need for a constitutive law that is accurate (i.e., it approximates well the behavior of the in-vivo myocardium tissue), numerically stable, and observable (i.e., its parameters can be estimated from clinical data). Exponential laws are usually more stable than their linear counterparts. Thus, exponential laws are given preference in the present embodiment, in particular the well known "Guccione law", "Costa law". For both models, the stress-strain energy is defined by an exponential relation:

$$W = \tfrac{1}{2}C(\exp(DQ)-1), \quad (6)$$

where C and D are parameters controlling the stiffness of the tissue and Q is an expression that describes the non-linearity of the model.

The model proposed by Guccione and colleagues in Guccione et al., "Mechanics of active contraction in cardiac muscle: Part II—Cylindrical models of the systolic left ventricle", *Journal of biomechanical engineering*, Vol. 115 (1), 82, 1993, considers the anisotropy along the fiber orientation only:

$$Q = b_1 E_{ff}^2 + b_2(E_{cc}^2 + E_{rr}^2 + 2E_{cr}E_{rc}) + 2b_3(E_{fc}E_{cf} + E_{fr}E_{rf}) \quad (7)$$

In this equation, E are the components of the Lagrangian strain tensor $E = (E_{ij})_{i,j}$, with f being the fiber direction, c the cross fiber direction, and r the radial direction. This model depends on three parameters, $b_1$, $b_2$ and $b_3$. Costa and colleagues, in Costa et al., "Modeling cardiac mechanical properties in three dimensions", *Philosophical Transactions A*, 359(1783):1233, 2001, improved that model to include the effect of myocardium sheet:

$$Q = c_1(E_{ff}^2) + c_2(E_{ss}^2) + c_3(E_{nn}^2) + 2c_4(E_{fs}E_{sf}) + 2c_5 (E_{fn}E_{nf}) + 2c_6(E_{sn}E_{ns}) \quad (8)$$

In practice, the parameters $b_i$ and $c_i$ are not adjusted to patient data but rather fixed from ex-vivo experiments. The modeler then adjusts the parameters C and D to fit the model to the data.

In an advantageous implementation, the present inventors have developed a hyperelastic Mooney-Rivlin model to model the passive properties of the myocardium tissue. Mooney-Rivlin models are well known and have been extensively used in mechanical engineering to simulate rubber-like materials. A key advantage of the Mooney-Rivlin model is its availability in a large variety of finite-element solutions, which enabled the present inventors to quantitatively verify this implementation. The Mooney-Rivlin model is a hyper-elastic material model whose strain energy density function is:

$$W = C_1\left(J^{-\tfrac{2}{3}}I_1 - 3\right) + C_2\left(J^{-\tfrac{4}{3}}I_2 - 3\right) + D_1(J-1)^2. \quad (9)$$

In this equation, $C_1$, $C_2$ and $D_1$ are free parameters, J is the Jacobian determinant of the deformation gradient $j = \det(\nabla\varphi)$, and $I_1$ and $I_2$ are the first and second invariants of the right Cauchy-Green deformation tensor $C = \nabla\varphi^T \nabla\varphi$, $I_1 = \text{tr}(C)$, $$I_2 = \frac{1}{2}(\text{tr}(C)^2 - \text{tr}(C^2)).$$

The standard approach to solving Equation (9) consists in deriving W with respect to C to compute the second Piola-Kirchhoff stress tensor of the internal forces. However, calculating that derivative may become computationally demanding as it involves the inversion of C for every element of the mesh. Instead, an efficient but accurate algorithm called Multiplicative Jacobian Energy Decomposition (MJED) can be used to compute non-linear tissue deformations. The underlying idea is to decompose the strain energy density function as:

$$W = \sum_k f^k(J) g^k(I) \quad (10)$$

where I is the vector of invariants ($I_1$, $I_2$, $I_4$, ...). The advantage of this decomposition is that the derivative of the invariants $g^k(I)$ does not involve the Jacobian determinant J anymore, thus resulting in more efficient numerical schemes to compute the stiffness matrix. Furthermore, the dynamic system is expressed in a total Lagrangian framework. As a result, most of the variables can be pre-computed at initialization, which further speeds up the computation.

Decomposing the Mooney-Rivlin model gives (the constants are not reported as they disappear in the computations):

$$f^1(J) = J^{-2/3} \quad g^1(I) = C_1 I_1$$

$$f^2(J) = J^{-4/3} \quad g^2(I) = C_2 I_2$$

$$f^3(J) = (J-1)^2 \quad g^3(I) = D_1 \tag{11}$$

Finite element methods based on linear tetrahedra can be used to compute the total force generated by the model. The heart anatomy is meshed with tetrahedral elements. Let T be an element whose vertex positions are ($P_i$) i=(1, 2, 3, 4) at rest and ($Q_i$) after deformation. For Euler implicit time discretization, two quantities must be computed: the nodal force $F_i$ and the stiffness matrix $K_{ij}$ defined at every edge ($Q_i, Q_j$):

$$F_i = -\left(\frac{\partial W}{\partial Q_i}\right)^T \quad K_{ij} = \frac{\partial^2 W}{\partial Q_j \partial Q_i} \tag{12}$$

The nodal force $F_i$ can be expressed as:

$$F_{h,i} = -V_0 \sum_{k=1}^{n} \left( f^{k'}(J) g^k(\tilde{I}) \left(\frac{\partial J}{\partial Q_i}\right)^T + f^k(J) \nabla \phi S_h^k D_i \right) \tag{13}$$

where $$S_h^k = 2 \frac{\partial g^k(I)}{\partial C},$$

$V_0$ is the volume of T at rest and Di is the shape vector associated to Qi. As it can be seen, this expression is generic and is valid for any model that can be decomposed according to Equation (10). For Mooney-Rivlin model we have:

$$f^{1'}(J) = -\tfrac{2}{3} J^{-5/3} \quad S^1 = C_1 Id$$

$$f^{2'}(J) = -4/3 \, J^{-7/3} \quad S^2 = C_2 (Id I_1 - C)$$

$$f^{3'}(J) = 2(J-1) \quad S^3 = 0 \tag{14}$$

Id is the identity matrix. The expression of the stiffness matrix $K_{ij}$ is more complex and can be expressed as:

$$K_{ij} = \frac{\partial^2 W(T_P)}{\partial Q_i \partial Q_j} = V_0 \sum_k (G^k + H^k + I^k + \Lambda^k + M^k + R^k), \tag{15}$$

where:

$$G^k = \left(\frac{\partial f^{k'}(J)}{\partial Q_i}\right)^T \frac{\partial J}{\partial Q_i} g^k(\tilde{I}) \quad \Lambda^k = \left(\frac{\partial f^k(J)}{\partial Q_j}\right)^T D_i^T S_h^k \nabla \phi^T \tag{16}$$

$$H^k = f^{k'}(J) \frac{\partial^2 J}{\partial Q_j \partial Q_i} g^k(\tilde{I}) \quad M^k = f^k(J) D_i^T S_h^k \left(\frac{\partial \nabla \phi^T}{\partial Q_j}\right)^T$$

$$I^k = f^{k'}(J) \left(\frac{\partial g^k(I)}{\partial Q_j}\right)^T \frac{\partial J}{\partial Q_i} \quad R^k = f^k(J) \left(\frac{\partial S_h^k}{\partial Q_j} D_i\right)^T \nabla \phi^T.$$

To calculate $K_{ij}$, the second derivative of $f^k$ (J) and the derivative of $S^k$ with respect to $Q_i$ must be calculated. The second derivatives of $f^k(J)$ are straightforward:

$$f^{1''}(J) = 10/9 J^{-8/3}$$

$$f^{2''}(J) = 28/9 J^{-10/3}$$

$$f^{3''}(J) = 2 \tag{17}$$

For the other derivative, it can be demonstrated that $$\frac{\partial S}{\partial Q_j} D_i = \sum_{v=1}^{3} \frac{\partial S}{\partial Q_j^v} D_i \otimes e_v, \tag{18}$$

where $e_v$ is the unit vector along X- (v=1), Y- (v=2) or Z-axis (v=3). $\partial S/\partial Q_j^v$ is the contraction of the fourth-order tensor $\partial S/\partial C$ with a second-order tensor M defined by $$\frac{\partial S}{\partial Q_j^v} = \frac{\partial S}{\partial C} : [D_j \otimes (\nabla \phi^T e_v) + (\nabla \phi^T e_v) \otimes D_j].$$

Applying these calculations to the Mooney-Rivlin model results in:

$$\partial S^1 / \partial Q_j \, D_i = 0 \tag{19}$$

$$\partial S^2 / \partial Q_j \, D_i = \sum_{v=1}^{3} (tr(M) Id - M) D_i \otimes e_v$$

$$\partial S^3 / \partial Q_j \, D_i = 0$$

For computational efficiency and memory optimization, the stiffness matrix $K_{ij}$ is stored for every edge of the mesh. Its contribution to each node is deduced by using the principle of action-reaction, i.e. $F_{1 \to 2} = -F_{2 \to 1}$, and the remarkable identity $\Sigma_i D_i = 0$. This technique can also be extended to handle anisotropic tissue properties and adapted to the Costa and Guccione laws as well as the Holzapfel law. Accordingly, it is to be understood that various constitutive laws may be used for modeling the passive properties of the myocardial tissue and the present invention is not limited to a particular law.

In an advantageous implementation, tissue passive properties (modeled using co-rotational elasticity or a non-linear Mooney-Rivilin model) can be personalized by using the observed cardiac motion during diastole. Inverse problem algorithms are used to estimate the tissue stiffness that minimizes the differences between simulation and observations.

Figure 8:
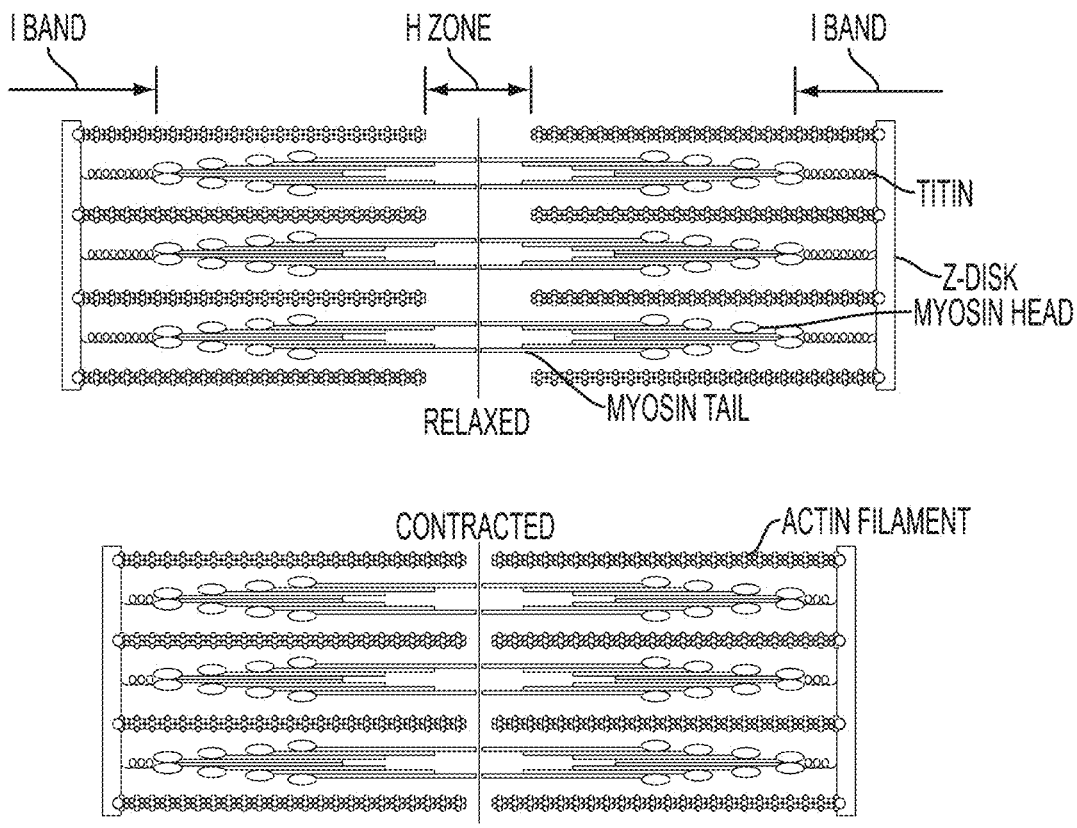
FIG. 8 illustrates a sliding model of cell contraction.

The second element of the biomechanical model mimics the active force generated by every cell when it depolarizes, which fades out once the cell repolarizes. The contraction is mainly generated by two proteins, the actin and the myosin, as illustrated in FIG. 8. FIG. 8 illustrates a sliding model of cell contraction. As illustrated in FIG. 8, actin filaments slide on top of the myosin protein during contraction.

Three categories of active contraction models can be distinguished. Biophysical models simulate the ion interactions and the actin-myosin bindings that generate the cardiac motion. Such models are highly detailed, governed by dozens of equations derived from experimental studies on ex-vivo animal hearts and controlled by a large number of parameters. Hence, biophysical models have been used for hypothesis testing mainly. Multi-scale phenomenological models mathematically integrate the biological mechanisms spanning from the actin-myosin interaction to the organ. The transition from one scale to another (from the calcium concentration to actin-myosin binding for instance) is mathematically achieved, ultimately resulting in a set of simplified equations that are controlled by fewer parameters (usually 4 to 5 parameters), with clinical meaning. Finally, lumped models focus on one single myocyte and do not consider the spatial dimension. These models can be solved very efficiently but they cannot capture regional abnormalities of the myocardium in patients, like scars or localized fibrosis for instance.

A target of the present invention is to simulate CRT from patient data. It is therefore important to have a model that is controlled by few parameters that can be measured, or estimated, from clinical data. Moreover, embodiments of the present invention simulate the cell mechanical response according to an electrical stimulus. Accordingly, embodiments of the present invention do not model all sub-cellular interactions giving rise to contraction but rather implement multi-scale approaches, which integrate these mechanisms in simpler equations. In particular, it is assumed in embodiments of the present invention that active contraction is directly related to the action potential through a multi-scale, linear law that relates the trans-membrane voltage with the rates of ATP binding and release.

In a first embodiment, a linear simplification of a phenomenological model is utilized to model the myocyte contraction. Advantages of this embodiment include few clinically-related parameters and computational efficiency, which enables personalization from clinical data. The active force is controlled by a switch function u(t) related to the depolarization time $T_d$ and the repolarisation time $T_r$ computed from the electrophysiology module. When the cell is depolarized ($T_d < t < T_r$), u(t) is constant and equals $+k_{ATP}$, the contraction rate. When the cell is repolarized ($T_r < t < T_d + HP$, HP is the heart period), u(t) equals $-k_{RS}$, the relaxation rate. The active stress $\sigma_c(t)$ of the cell is computed from u(t) according to:

$$\frac{d\sigma_c(t)}{dt} + |u(t)|\sigma_c(t) = |u(t)|_+ \sigma_0, \quad (20)$$

where, $\sigma_0$ is the maximum asymptotic contraction and $|u(t)|_+$ is the positive part of the command function u(t). The analytical resolution of this equation writes:

$$\begin{cases} \text{if } T_d \le t \le T_r: & \sigma_c(t) = \sigma_0[1 - e^{+k_{ATP}(T_r - t)}] \\ \text{if } T_r < t < T_d + HP: & \sigma_c(t) = \sigma_c(T_r)e^{-k_{RS}(T_r - t)}. \end{cases} \quad (21)$$

Figure 9:
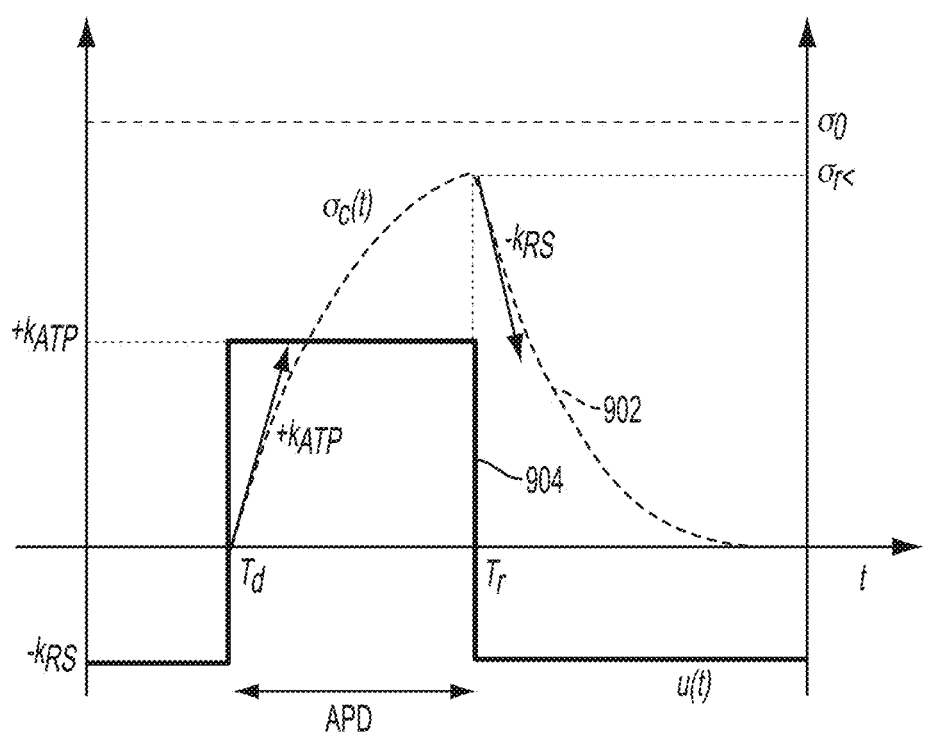
FIG. 9 illustrates variation of the active contraction stress with respect to the electrical command signal.

The parameters $k_{ATP}$ and $k_{RS}$ are therefore directly related to the myocardium stress: they control the contraction and relaxation rates respectively. FIG. 9 illustrates variation of the active contraction stress $\sigma_c(t)$ 902 with respect to the electrical command signal u(t) 904, which is computed by the electrophysiology module.

In a second embodiment, a simplified representation of a cross-bridge cycle mechanism is used as multi-scale model of active myocyte contraction. This model is more detailed as the one used in the first embodiment and provides more degrees of freedom. The model is an extension of a model that carefully handles energy balance and the chemical cycles giving rise to cell contraction. Moreover, the model is directly related to cardiac electrophysiology through a switch function that is controlled by the trans-membrane potential, and not [Ca2+] concentration, which makes the use of phenomenological or Eikonal models of cardiac electrophysiology possible. That switch function lumps all sub-cellular mechanisms involved in electromechanical coupling (Calcium-Induced-Calcium-Release, Ca2+ pump mechanisms, etc.).

The model focuses on the simplified representation of cross-bridge cycle mechanism. When Ca2+ is released, it binds to the troponin complex, which slides and makes visible the actin binding site. The myosin head binds to the actin, ATP is phosphorized and the myosin head rotates (from 90 to 45 degrees approximately), thus generating an active mechanical stress. Then, the myosin head hydrolizes the ATP, unbinds, and rotates back to its initial configuration. The cycle is repeated as long as ATP and Ca2+ are available. This chemical cycle can be translated into a mechanical cycle and integrated at the sarcomere level using Huxley's method. The concentration of available actinmyosin pairs with those already binded (cross-bridges) are related to the molecular 1D strain by assuming rigid actin and myosin filaments. The law of parallel springs is then used to get a model of the whole collection of myosin molecules in the sarcomere:

$$\frac{\partial n}{\partial t} + \dot{e}_c \frac{\partial n}{\partial s} = (n_0 - n)f - ng, \quad (22)$$

$$\tau_c(t) = \int \frac{\partial W_m(t,s)}{\partial s} n(t,s)ds,$$

where n is the density of existing actin/myosin bridges at a given time t and strain s, $\dot{e}_c$ is the macroscopic filament sliding rate, which is equal to the strain rate s' under the rigid filament assumptions, $n_0$ is a time-varying reduction factor modeling the fact that not all bridges can actually bind. $f$ and $g$ are binding and unbinding rate functions, $W_m$ is the microscopic mechanical energy and $\tau_c$ is the microscopic active stress.

In this model, actin-myosin bridges are modeled as linear springs with stiffness $k_0$ and pre-strain $s_0$, such that the energy $W_m$ can be expressed as $W_m(t,s) = k_0/2(s+s_0)^2$. The binding and unbinding rates $f(t,s)$ and $g(t,s)$, respectively, are directly controlled by cardiac electrophysiology according to the equations:

$$f(t, s) = k_{ATP} \mathbb{1}_{s \in [0,1]} \mathbb{1}_{[Ca^{2+}] > C},$$ (23)

$$g(t, s) = \alpha |\dot{e}_c| + k_{ATP} \mathbb{1}_{s \in [0,1]} \mathbb{1}_{[Ca^{2+}] > C} + k_{RS} \mathbb{1}_{[Ca^{2+}] < C}.$$

$$u(t) = |u(t)|_+ - |u(t)|_- \text{ with } \begin{cases} |u(t)|_+ = k_{ATP} \mathbb{1}_{[Ca^{2+}] > C} \\ |u(t)|_- = k_{RS} \mathbb{1}_{[Ca^{2+}] < C} \end{cases}$$

$$f(s, t) = |u(t)|_+ \mathbb{1}_{s \in [0,1]},$$

$$g(s, t) = |u(t)| + \alpha |\dot{e}_c| - f(s, t).$$

where $k_{ATP}$ and $k_{RS}$ are two constants, $1_{[Ca2+]}$ is the characteristic function of calcium concentration, directly related to the trans-membrane potential through an activation threshold $v_{threshold}$, and $\alpha$ is a constant that controls the amount of bridges destructed due to high strain rate. These equations are integrated at the organ scale using moments, which yields the following ordinary differential equations:

$$\begin{cases} \dot{k}_c = -(|u| + \alpha |\dot{e}_c|)k_c + n_0 k_0 |u|_+ \\ \dot{\tau}_c = -(|u| + \alpha |\dot{e}_c|)\tau_c + \dot{e}_c k_c + n_0 \sigma_0 |u|_+ \end{cases}$$ (24)

Finally, a viscous term is added to the microscopic stress $\tau c$ to account for energy dissipation due to friction and viscous effects, yielding the final active stress:

$$\sigma_c = \tau_c + \mu \dot{e}_c.$$

Figure 10:
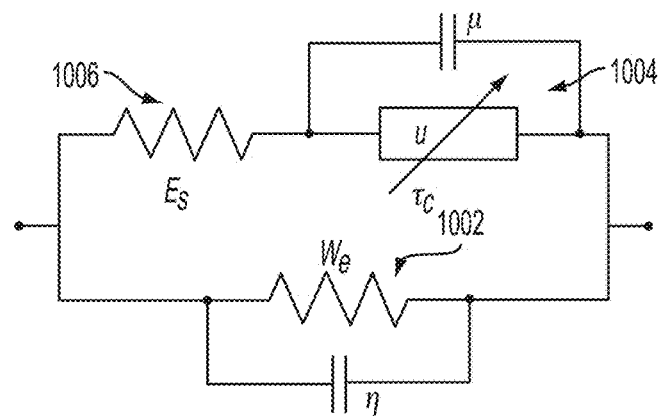
FIG. 10 illustrates a Rheological model of cardiac biomechanics.

The active model of cell contraction described by the previous equation is integrated into the global heart model using a Hill-Maxwell rheological analogy. FIG. 10 illustrates a Rheological model of cardiac biomechanics. As illustrated in FIG. 10, Three elements constitute the Rheological model: a passive, parallel element $W_e$ 1002, which models the tissue properties due to the collagen matrix in particular; and two elements 1004 and 106 in series. $e_c/\sigma_c$, is the macroscopic active force previously described. $E_s$ 1006 is an additional elastic element that describes the Z disks. This element is crucial to model isometric behavior (when active stress results in no strain). Combining the two series elements 1004 and 1006 results in the following ODE's, which are solved within the organ domain to simulate cardiac contraction:

$$(\tau_c + \mu \dot{e}_c)(1 + 2e_c)^3 = E_s(e_{1D} - e_c)(1 + 2e_{1D})$$

$$\dot{k}_c = -(|u| + \alpha |\dot{e}_c|)k_c + n_0 k_0 |u|_+$$

$$\dot{\tau}_c = -(|u| + \alpha |\dot{e}_c|)\tau_c + \dot{e}_c k_c + n_0 \sigma_0 |u|_+.$$ (25)

In these equations, $e_{1D}$ is the 1D fiber strain.

It can be noted that because the mathematical derivations of this model carefully handled the amount of ATP being used by the system, the energy balance is controlled during the cardiac cycle. This model thus enables one to relate cardiac contraction with oxygenation for instance through the time varying parameter $n_0$.

Different numerical schemes have been implemented to integrate the ODE's such as Euler explicit scheme, exponential explicit scheme for increased robustness, and prediction/correction Euler implicit scheme. Preliminary quantitative analyses of these different schemes showed no significant numerical differences ($<10^{-1}$ mm) with a standard mechanical time stepping of $10^{-3}$s. Accordingly, any method for integrating the ODE's may be used.

In an advantageous implementation, active contraction strength $\sigma_0$ is personalized (in the first or second embodiment) by using the observed cardiac motion from the images during systole and measured ejection fraction. Inverse problem algorithms are used to estimate this parameter such that differences between simulation and observations are minimized.

The two components of the biomechanical model (passive and active) are solved on the patient's anatomy using finite element methods. The motion of the heart resulting from these laws is computed by solving the dynamic system for all the vertices of the mesh:

$$M\ddot{U} + C\dot{U} + KU = F_c + F_p + F_b,$$ (26)

where U is the displacement vector of the mesh vertices, U' is their velocity and Ü their acceleration. M is the diagonal mass matrix. Mass lumping is used with a mass density of $\rho = 1.07$ g/mL. C is a Rayleigh damping matrix (C=0.1M+0.1K). K is the anisotropic linear elastic stiffness matrix calculated using the model for the passive properties of the myocardium. $F_p$ captures the pressures applied to the endocardia during the various cardiac phases. $F_b$ accounts for the external boundary conditions. Finally, $F_c$ is the active force generated by the depolarized cells. For a given tetrahedron with fiber direction f (f is a column vector), the active stress $\sigma_c(t)$ results in a 3D anisotropic stress tensor $\Sigma(t) = \sigma_c(t) ff^T$, from which we get the contraction force vector per tetrahedron:

$$F_c = \int \Sigma(t) n dS$$ (27)

where S is the outer surface of the tetrahedron and n the surface normal. The previous equation is discretized in time and space using finite element and semi-implicit schemes, resulting in the linear system:

$$\Xi U = F,$$ (28)

where $\Xi$ is the system stiffness matrix and F the accumulated forces. The linear system can be solved using conjugated gradient method.

The cardiac electrophysiology and biomechanics are solved simultaneously. At each iteration, the EP model is first computed. The new potential value is then used to compute the active force generated by the cell. The process is iterated to compute cardiac electromechanics over time.

Returning to FIG. 3, the boundary condition module 326 estimates patient-specific boundary conditions of the LV and RV. Heart function depends on external conditions mostly determined by neighboring organs, the blood flow and the circulatory system. Neighboring organs play a pivotal role in cardiac mechanics. Heart ventricles are connected to the atrium and arteries, which create some additional stiffness at the valve plane. One possible way to model these effects is to add some additional stiffness in the base/valve region using stiff springs.

Blood flow is modeled using fluid structure interaction (FSI) methods. These approaches are very detailed but also complex to solve, with coupled systems controlled by large sets of parameters. Alternatively, only the ventricular pressure is considered and applied as constraints of the biomechanical model. The constraints are computed from lumped models of the circulatory system or directly input by the user. These approaches rely on clinically related parameters and are fast to compute but ignore the flow patterns in the ventricles, which may have long-term impact on the cardiac function or on the effects of a therapy.

Flow patterns inside the ventricle are assumed to have minor effect on the acute outcome of CRT, just after the intervention. Accordingly, embodiments of the present invention model the hemodynamics parameters using lumped parameters (homogeneous intraventricular pressures) within each chamber; model arterial pressure using a lumped Windkessel model; model atrial pressure using a lumped model; decouple the heart module from the entire circulatory system for computational tractability and model personalization; and model the cardiac phases as sequential states (i.e., the model cannot come back to the previous phase).

Figure 11:
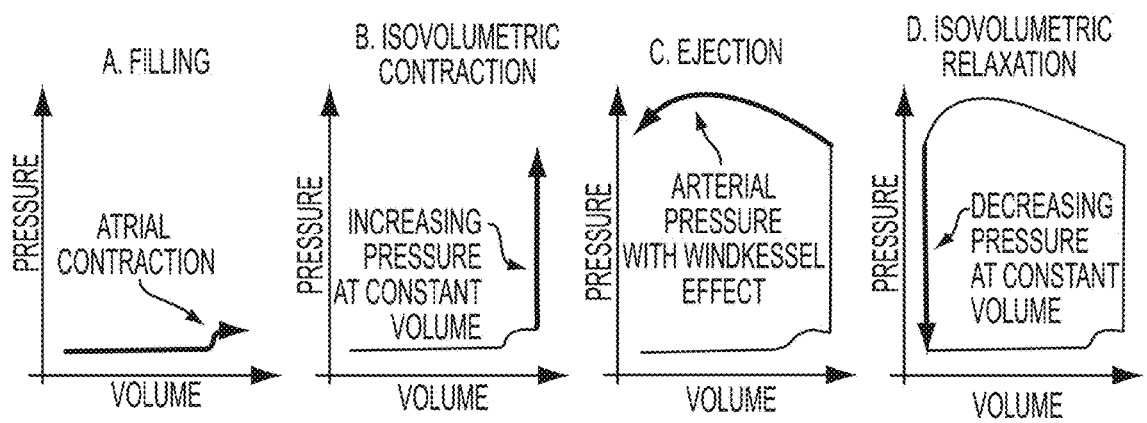
FIG. 11 illustrates the four cardiac phases.

The four cardiac phases of filling, isovolumetric contraction, ejection and isovolumetric relaxation are simulated by alternating the boundary conditions of the model according to the following rules. FIG. 11 illustrates the four cardiac phases. When the flow, computed as the derivative of chamber volume, is positive and the ventricular pressure is equal to the atrial pressure, the ventricle is filling, as illustrated in image A of FIG. 11. A pressure equal to the atrial pressure is applied to the endocardial surface to mimic the active filling. As soon as myocardial cells start to contract, the blood flow is reverted, and the atrioventricular valve closes. Yet, the pressure is still lower than the arterial pressure, the arterial valves stay closed. The ventricular volume thus stays constant: this phase is called isovolumetric (or isochoric) contraction phase, as illustrated in image B of FIG. 11. A new projection/prediction constraint is employed to compute the ventricular pressure during this phase while ensuring constant ventricular volume. When the penalty pressure becomes higher than the arterial pressure, the aortic valve opens and the blood is ejected, as illustrated in image C of FIG. 11. The pressure of the artery is applied to the endocardial surfaces to mimic the resistance of the vessels on the cardiac contraction. As soon as the ventricle starts to relax, the blood flow is reverted. The arterial valve closes and this phase is called the isovolumetric relaxation phase, as illustrated in image D of FIG. 11. A new projection/prediction constraint is employed to compute the ventricular pressure during this phase while ensuring constant ventricular volume. During each phase, the pressure applied to the endocardial surfaces is computed for each vertex and gathered into the global pressure vector $F_p$ of the dynamic systems. The phases are handled independently for the left and right ventricles to be able to capture asynchronous cardiac motions. This is a crucial feature for CRT planning.

Figure 12:
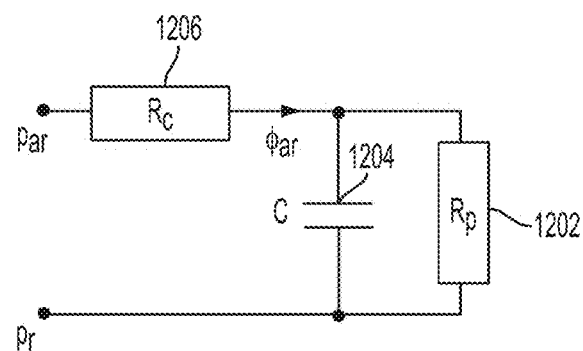
FIG. 12 illustrates a circuit analogy of a 3-element Windkessel model.

The arterial pressure is modeled using a 3-element Windkessel model, which takes as input the arterial flow and returns the pressure within the artery at every time step of the simulation. The model is derived from electrical circuit analogies where the blood flow is the current and the arterial pressure is the voltage. FIG. 12 illustrates the circuit analogy of the 3-element Windkessel model. As illustrated in FIG. 12, the first element of the model is a peripheral resistance $R_p$ 1202, which accounts for the distal resistance of the circulatory system mainly due to the small vessels. The compliance C 1204 accounts for the elasticity of the arterial walls whereas the characteristic resistance $R_c$ 1206 accounts for the blood mass and for the compliance of the artery proximal to the valves. Let $\varphi_{ar}(t)$ be the arterial flow at time $t$, defined as the opposite of the ventricular flow, $p_{ar}(t)$ be the arterial pressure at time $t$ and $p_r$ be a constant low pressure of reference (typically the pressure of the remote venous system). When the blood flows into the arteries ($\varphi_{ar}(t)>0$), during ejection, the 3-element model can be expressed as:

$$\frac{dp_{ar}(t)}{dt} = R_c \frac{d\Phi_{ar}(t)}{dt} + \left(1 + \frac{R_c}{R_p}\right)\frac{\Phi_{ar}(t)}{C} - \frac{p_{ar}(t) - p_r}{R_p C}. \quad (29)$$

When the valves are closed, the blood flow is stopped ($\varphi_{ar}(t)=0$) and the model can be expressed as:

$$\frac{dp_{ar}(t)}{dt} = -\frac{p_{ar}(t) - p_r}{R_p C}. \quad (30)$$

These equations are integrated using first-order implicit schemes. Two independent Windkessel models are used for the aorta and the pulmonary artery.

Atrium contraction, which happens just after diastases and before systole, optimizes ventricular filling. Because simulating atrial contraction explicitly in 3D may be computationally demanding, a possible approach is to rely on lumped models that mimic the raise of ventricular pressure due to atrial contraction. While some simplified models consider atrial pressure constant, it is also possible to use phenomenological models of atrial pressure based on sigmoid functions. More predictive elastance models have also been proposed to capture the interactions between atrial volume, pressure, tissue stiffness and circulatory system.

In an embodiment of the present invention, a simplification of a circulatory model is used to model the atrium boundary conditions. In particular, the arteries are decoupled from the atria and pulmonic and systemic circulations are neglected. Atrial contraction is modeled using a lumped time-varying elastance model. Minimum and maximum elastance parameters enable the peak systolic and diastolic stiffness to be set, which then controls atrial pressure based on the current volume. A simple model of atrial activation, synchronized with the ventricular electrophysiology model through a time-shift parameter corresponding to the ECG PQ interval, enables controlling of the atrial volume. In this implementation, vena cava and pulmonic veins are kept constant throughout the cardiac cycle. The user can manually adjust them to control the baseline pressure of the atrium.

For both atria, the pressure is computed according to the following equation (only left atrium LA is provided below, similar equations are used for the right atrium):

$$p_{LA} = E_{LA} \times (V_{LA} - V_{LA,rest}), \quad (31)$$

where the elastance $E_{LA}$ and the rest volume $V_{LA,rest}$ are:

$$E_{LA} = (E_{LA,max} - E_{LA,min}) \times y_a + E_{LA,min}$$

$$V_{LA,rest} = (1-y_a)(V_{LA,rd} - V_{LA,rs}) + V_{LA,rs}. \quad (32)$$

In these equations, $E_{LA,max}$, $E_{LA,min}$, $V_{LA,rd}$, and $V_{LA,rs}$ are free parameters of the model (maximum and minimum elastance, and diastolic and systolic volumes at zero pressure, respectively). $y_a$ is an activation function defined by:

$$y_a = \begin{cases} -12\cos(2\pi t_{atrium}/t_{twitch}) + 0.5 & t_{atrium} < t_{twitch} \\ 0 & t_{atrium} \geq t_{twitch} \end{cases}, \quad (33)$$

where $t_{twitch}$, is the duration of the ventricular contraction and:

$$t_{atrium} = \begin{cases} \mod(t - t_{active} + \Delta t_{PR}, t_{cycle}) & t \geq t_{active} - \Delta t_{PR} \\ 0 & t < t_{active} - \Delta t_{PR} \end{cases}. \quad (34)$$

The volume of the left atrium is given by integrating the ordinary differential equation (ODE):

$$\frac{dV_{LA}}{dt} = Q_{vp} - Q_{mitral}, \quad (35)$$

where $Q_{mitral}$, the flow through the mitral valve, is equal to the volume variation of the 3D ventricle during systole, and $Q_{vp}$, the flow through the pulmonary vein, is given by:

$$Q_{vp} = (p_{vp} - p_{LA})/R_{vp}, \quad (36)$$

where $p_{vp}$ is the pulmonary vein pressure and $R_{vp}$ is the resistance of the pulmonary veins. These equations can be solved using a first-order Euler implicit scheme for numerical stability. Two independent models are used for the left and for the right atria.

During the isovolumetric contraction and relaxation phases, ventricular pressure varies under myocardium motion but the ventricular volume stays constant. During these phases, internal pressure builds up (isovolumetric contraction) or decreases (isovolumetric relaxation) sharply. As the internal volume does not change, the myocardium mainly twists, which improves ejection (or filling) efficiency. Simulating these phases accurately is therefore important to capture pathologies in myocardium mechanics, often characterized by inefficient isovolumetric phases. CRT outcome can also be quantified by the postoperative raise in pressure dp/dt, which is mainly happening during these phases.

A first possible strategy is to use a penalty pressure force $F_{iso}(t) = \int k_{iso}(V(t) - V_0)ndS$, where V(t) is the current volume at time t and $V_0$ is the volume at the beginning of the isovolumetric phase. This method is computationally efficient. The force, which acts as a pressure, can be computed very efficiently from the current state of the system. However, that approach requires small time steps to be stable. Considering the previous volume V(t−dt) instead of $V_0$ makes the method more robust to time stepping, but prone to error propagation and volume drifts. This last approach, available in the current framework, can be used as surrogate model of isovolumetric phases for parameter estimation as it is computationally efficient. The final simulation is then computed using the more accurate model described below.

More accurate models of isovolumetric phases have been proposed. One approach is to fill the ventricle cavity with finite elements, and constrain that domain to be incompressible using Lagrangian methods or high Poisson ratio. Other methods rely on Lagrangian methods to project, at the end of every time step, the position of the endocardial nodes such that the ventricular volume stays constant. An advantageous embodiment of the present invention provides a new method for modeling isovolumetric cardiac dynamics. Let $V_0$ be the endocardial volume at the beginning of the isovolumetric phase, U(t) is the displacement vector X(t)−X(t=0) at time t, $\Xi$ is the system stiffness matrix (Equation 28) at time $_t$, p(t) is the first estimate of ventricular pressure at t and dt the time step. The embodiment of the present invention relies on a prediction/correction approach.

First, the current pressure estimate p(t) is corrected such that endocardial volume is preserved. To that end, the dynamics system of Equation 28 is solved without constraint to compute the new, unconstrained position $\hat{X}(t+dt)$ given p(t). The positions $\hat{X}(t+dt)$ are then projected to get a final position X(t+dt) such that $V(t+dt) = V_0$. This amounts to finding a corrective displacement δ along the surface normal n to move $\hat{X}(t+dt)$ such that $V(t+dt) = V_0$. In order to calculate the corrective pressure that results in such a displacement, let λ(t) be the corrective pressure to add to the current pressure estimate p(t). If λ(t) is known, then the dynamics system can be expressed as $\Xi U = F + \lambda N$ where N is the vector gathering the lumped area vectors ndS of the endocardial surfaces corresponding to the corrective pressure force $\int \lambda(t) ndS$. λ is equal to zero for the internal nodes. Solving the system at $_t$ yields $U(t+dt) = \Xi^{-1}F + \lambda \Xi^{-1}N$. However, $\Xi^{-1}F = \hat{U}(t+dt)$, which is known. Thus, the constrained system is:

$$\begin{cases} X(t+dt) = \hat{X}(t+dt) + \lambda \Xi^{-1}N \\ V(t+dt) = V_0 \end{cases} \quad (37)$$

$\Xi^{-1}N$ is computed by solving the system $\Xi A = N$ It can be shown that λ is actually the Lagrangian multiplier of Equation 37. λ(t) and X(t+dt) can therefore be solved very efficiently and locally for each vertex by solving a third-order polynomial, The corrective displacement is performed along $\Xi^{-1}n$ and not n, thus considering the dynamics of the system. The system is only solved twice to compute the intermediate position $\hat{X}(t+dt)$ and the direction of the corrective displacement $\Xi^{-1}n$.

After the correction step, the endocardial nodes are projected such that the ventricular volume is preserved. The final, corrected pressure corresponding to this displacement is $\tilde{p}(t) = p(t) + \lambda(t)$. The pressure at the next time step is then predicted. To that end first order Taylor expansion can be used:

$$p(t+dt) = \tilde{p}(t) + dt \frac{d(\tilde{p})}{dt} = 2(p(t) + \lambda(t)) - \tilde{p}(t-dt), \quad (38)$$

where $\tilde{p}(t-dt)$ is the corrected pressure at t−dt. Higher-order expansions are also available in various embodiments for more accurate predictions.

Figure 13:
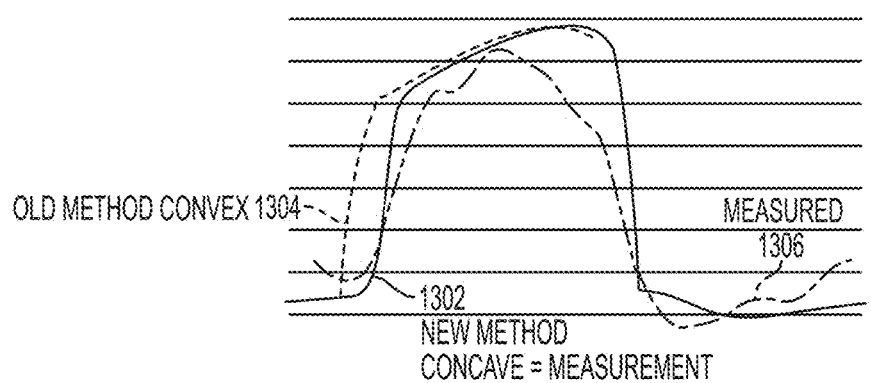
FIG. 13 illustrates improvements obtained using the prediction/correction model of isovolumetric phases according to an embodiment of the present invention.

FIG. 13 illustrates improvements obtained using the prediction/correction model of isovolumetric phases according to an embodiment of the present invention. As illustrated in FIG. 13, the simulated pressure 1302 using the prediction/correction model of isovolumetric phases and simulated pressure 1304 using the penalty approach are shown. The simulated pressure 1302 using the prediction/correction model follows more closely to the measured pressure 1306. FIG. 13 illustrates the improvements obtained using the proposed isovolumetric constraint. The raise and decrease in pressure 1302 during the isovolumetric contraction and relaxation, respectively, is more realistic and better matches the measured pressure 1306. In particular, the raise in pressure 1302 presents a concave shape as observed in reality, which cannot be achieved using the penalty constraints. Another advantage of this method is that it has no free parameters. The ventricular pressure is directly related to the myocardium motion and atrial/arterial boundary conditions.

Figure 14:
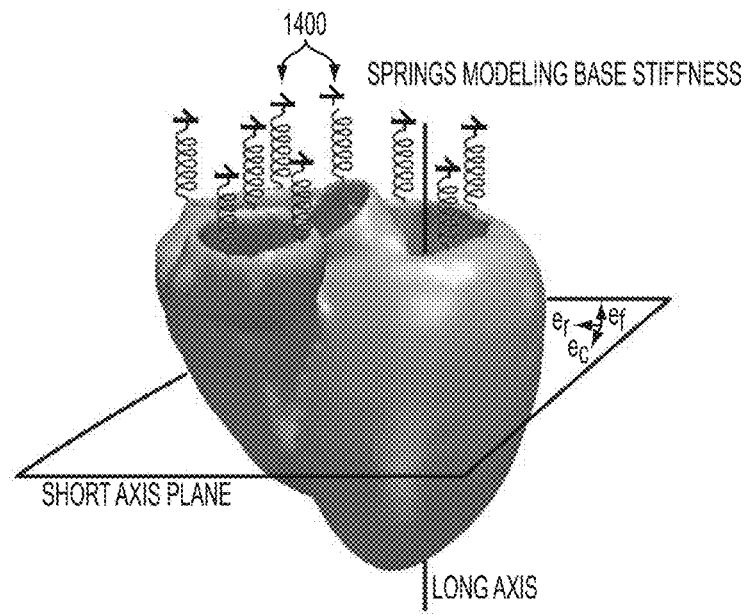
FIG. 14 illustrates modeling the effect of arteries and atria on the ventricular motion using a base stiffness parameter.

FIG. 14 illustrates modeling the effect of arteries and atria on the ventricular motion using a base stiffness parameter. As shown in FIG. 14, the effect of arteries and atria on the ventricular motion is simulated by connecting the vertices of the valve plane to springs 1400 whose stiffness is $K_{base}$. The fixed extremity of the springs 1400 corresponds to the rest position of the nodes, taken at mid diastasis, when the heart is at rest. The spring stiffness $K_{base}$ is anisotropic. A strong stiffness is applied along the long axis $e_l$ of the heart, while a lower stiffness is employed in the short axis plane ($e_r$, $e_c$)

to allow free radial motion. Under these definitions, the base stiffness force can be expressed as:

$$F_{base} = P \begin{pmatrix} K_{base_l} & 0 & 0 \\ 0 & K_{base_r} & 0 \\ 0 & 0 & K_{base_c} \end{pmatrix} P^{-1}(x - x_0), \quad (39)$$

where P is the transformation matrix going from the global coordinate system to the coordinate system defined by the LV long axis and the short axis plane, as illustrated in FIG. 14.

As an alternative to or in addition to the base stiffness parameter described above, a pericardium constraint may be used as a boundary constraint to model the effects of neighboring organs. Although it is possible to rely on a strong base stiffness parameter to fix the heart in the 3D space, computed cardiac motion highly depends on the strength of this boundary condition and also on the positions of the spring attachments. In reality, the effect of the great arteries and of the atrium on the bi-ventricular myocardium does not dominate the overall cardiac contraction. Indeed, the heart contracts longitudinally, the base moving downwards towards the apex. Anatomically, the heart and the root of the great vessels are protected by a stiff "sac", called pericardium, which fixes the heart to the diaphragm and the sternum. Heart motion is also constrained by the neighboring lungs and liver. On the other hand, the myocardium is free to move inside the pericardium bag. A thin layer of pericardial fluid separates the epicardium to the pericardium, allowing friction-free sliding of the myocardium.

Figure 15:
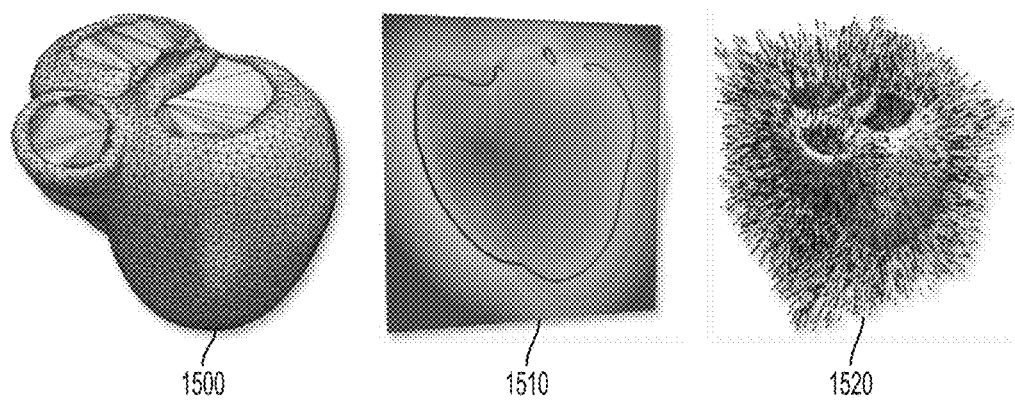
FIG. 15 illustrates generating a pericardium model according to an embodiment of the present invention.

In a possible implementation, a contact-based model of the pericardium can be used to mimic the effects of the neighboring organs and of the pericardium on the cardiac motion, while enabling one to fine-tune the stiffness of the great vessels and atria attachments to get realistic basal motion. The idea is to limit the motion of the epicardial nodes inside an authorized area while preserving friction-free sliding. FIG. 15 illustrates generating the pericardium model according to an embodiment of the present invention. As illustrated in image 1500, the epicardial domain is determined from the detected cardiac epicardium at end-diastole. Valve holes are automatically closed to define an inner and outer region. As shown in image 1510, a signed distance map from the epicardial boundary is generated to identify the interior and exterior of the pericardium bag. The distance map allows the epicardium to freely slide along the pericardial sac. Let D(x) be that distance map, where x is the spatial coordinate. D(x) is negative inside the pericardium sac, positive outside. As shown in image 1520, the normalized gradient map, grad D(x) is then computed. For each voxel x of the gradient map a normalized direction vector g(x) is determined which points towards the closest point of the epicardial contour. Based on this spatial information, the motion of the epicardial nodes can now be limited to a restricted zone. For example, the epicardial nodes can be restricted to move inside the pericardial sac only (identified by D(x)<0). This can be achieved by applying a force to every node that goes outside the pericardial sac to bring it back to the authorized area. The strength and direction of that force is computed from the gradient and distance map as follows:

$$\begin{cases} f(x) = 0 & \text{if } D(x) < 0 \\ f(x) = -k \dfrac{D(x)^2}{D(x)^2 + m^2} g(x) & \text{if } D(x) > d_{out} \end{cases}, \quad (40)$$

where x is the position of the node, k is the maximum strength of the force, m is the rate at which the force increases and $d_{out}$ is a parameter that enables to control the extent of the authorized area around the pericardial region. It should be stressed that f(x) is applied to the epicardial nodes only.

The model described by Equation 40 only controls the cardiac motion when the myocardium goes outside the authorized area. However, the pericardium can impact the inward radial displacement too, reducing the motion of the epicardium compared to the one of the endocardium. The present inventors thus improved Equation 40 to mimic this observation. The new pericardium constraint force becomes:

$$\begin{cases} f(x) = k \dfrac{D(x)^2}{D(x)^2 + m^2} g(x) & \text{if } D(x) < d_{in} \\ f(x) = -k \dfrac{D(x)^2}{D(x)^2 + m^2} g(x) & \text{if } D(x) > d_{out} \end{cases}. \quad (41)$$

The force is now symmetric, $d_{in}$ and $d_{out}$ control the extent of the authorized region. With this definition, the epicardial nodes can slide along the pericardium cavity, but their radial motion is limited to emulate neighboring organs and the stiff pericardial sac. It is also possible to select the epicardial nodes on which to apply the pericardium constraint. By default all epicardial nodes can be constrained but subsets can be selected to mimic different spatially varying boundary conditions.

The target of personalization of the parameters of the cardiac electrophysiological module (322), the cardiac biomechanical module (324) and the boundary conditions (326) is to determine the proper parameters for the different models to capture the observed volume variation, pressure curve, and heart dynamics observed in the medical images. FIG. 16 illustrates an algorithm for determining patient-specific parameters of the computational heart model according to an embodiment of the present invention. As illustrated in FIG. 16, at step 1601, the Windkessel parameters for the aorta and pulmonary artery are personalized using measured volume (from the dynamic images) and pressure curves (e.g., resulting from invasive pressure measurements). An exhaustive search approach can be used to determine the patient-specific parameters that best fit the observed data. At step 1602, the simulation is run with the adjusted (personalized) Windkessel parameters and default electromechanical parameters. At step 1603, the simulation is synchronized with the measured volume curve. In order to synchronize the simulation with the measured volume curve, the electrophysiological (EP) stimulus time $T_{init}$ is adjusted to match the atrial contraction time based on the measured volume curve, and the global APD duration is adjusted to match the systole duration in the measured volume curve. At step 1604, the simulated ejection fraction and wave form of ventricular volume are matched with measured values by adjusting the active contraction strength $\sigma_0$ and the parameters $k_{ATP}$ and $k_{RS}$ of the active biomechanical model. At step 1605, the LV pressure measurement is matched by adjusting $\sigma_0$ and E (Young's modulus), or related parameters of hyper-elastic models, as well as the pulmonary vein pressure to shift the left atrium baseline pressure towards the measured LV pressure. The personalization of the specific models are discussed in greater details below.

Cardiac Electrophysiology:

The cardiac electrophysiology model is personalized from the patient's ECG, dynamic images and, if available, endocardial mappings. If only ECG is available, simulated QRS is aligned with measured QRS by adjusting tissue diffusivity (parameter K in Equation 1). If endocardial mappings are available, inverse problem methods are used to estimate tissue conductivity and $\tau_{close}$ by comparing the simulated isochrones and potentials with measurements. Finally, dynamic images can be used to adjust electrophysiology overall synchrony by minimizing the difference of the cardiac motion computed from the electrophysiology model and the observations. Bundle branch blocks can be simulated by modifying the activation times of the left and right ventricles.

Cardiac Tissue Elasticity:

Tissue passive properties are personalized in this invention by using the observed cardiac motion during diastole. Inverse problem algorithms are used to estimate the tissue stiffness that minimizes the differences between simulation and observations.

Active Contraction:

Active contraction strength $\sigma_0$ is personalized in this invention by using the observed cardiac motion from the images during systole and measured ejection fraction. Inverse problem algorithms are used to estimate that parameter such that differences between simulation and observations are minimized.

Circulation Parameters:

If invasive pressure measurements are available, Windkessel parameters are directly estimated by simulating aortic pressure given the flow measured from the images and modifying the parameters such that the computed pressure matches the measurements. The ODE being relatively simple, its parameters can be uniquely estimated. If only pressure at peak systole is available, then only the characteristic resistance can be estimated.

Figure 17:
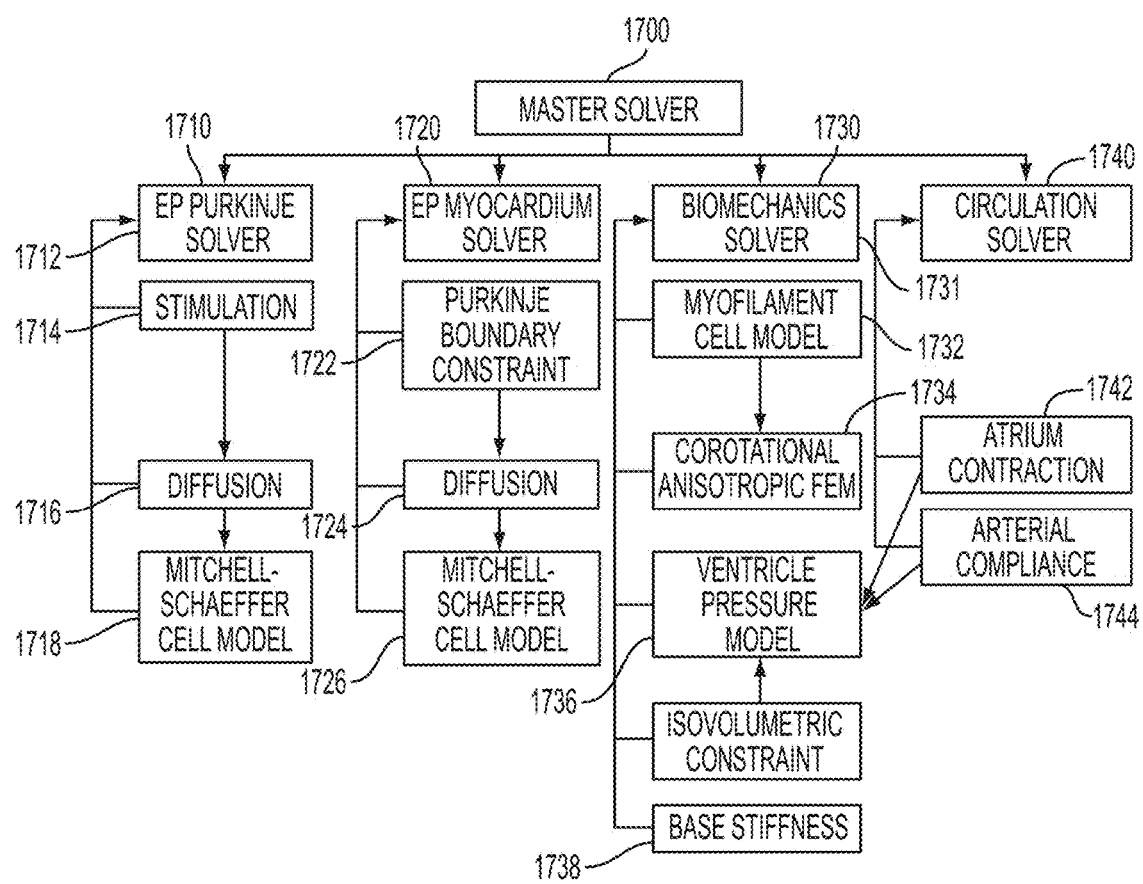
FIG. 17 is a block diagram illustrating the framework for simulating the heart function using the computational heart model according to an embodiment of the present invention.

FIG. 17 is a block diagram illustrating the framework for simulating the heart function using the computational heart model according to an embodiment of the present invention. This simulation is performed at step 320 of FIG. 3 (and step 220 of FIG. 2) and the simulation results are used to adjust the model parameters based on the observed image data and the measures patient data. The driving requirement of the system is modularity and reusability. Every component of the multi-scale computational model is designed independently, with data flowing between each component through memory as illustrated by the arrows in FIG. 17. In a possible implementation, the whole simulation can be set up through an XML file. Different models can therefore be tested in a simple way by just inter-changing the related components. Internally, the master solver 1700 orchestrates the whole simulation. At every time step, each sub-solver 1710, 1720, 1730, and 1740 (one for each physical phenomenon) is called sequentially. Before solving for the next time step, internal data is updated according to the dependencies. After every iteration, output data is dumped as requested by the user. Finally, model parameters are passed through the simulation XML file. Personalized model parameters for a patient are stored in the simulation XML file to be used for the CRT simulations.

In the embodiment of FIG. 17, the master solver 1700 sequentially calls an electrophysiological Purkinje solver 1710, an electrophysiological myocardium solver 1720, a biomechanics solver 1730, and a circulation solver 1740 at each time step. The electrophysiological Purkinje solver 1710 includes a stimulation component 1712, a diffusion component 1714, and an M-S cell model component 1716. The electrophysiological myocardium solver 1720 includes a Purkinje boundary constraint component 1722 (which imports the simulated potential from the Purkinje solver 1710 as a boundary condition), a diffusion component 1724, and a Mitchell-Schaeffer (M-S) cell model component 1724. The biomechanics solver 1730 includes a myofilament cell model component 1731 (active contraction), a co-rotational anisotropic FEM component 1732 (myocardium passive properties), a ventricle pressure model component 1734, an isovolumetric constraint component 1736, and a base stiffness component 1738. The circulation solver 1740 includes an atrium contraction component 1742 and an arterial compliance component 1744. It is to be understood that the models/components used in this embodiment are not limiting. For example, in various embodiments, the co-rotational anisotropic FEM component 1732 can be replaced by a Mooney-Rivlin or other hyper-elastic models, or the base stiffness component 1738 can be replaced by a pericardium constraint component, or both used jointly.

Returning to FIG. 1, at step 120, once the patient-specific parameters for the computational heart model are determined, CRT is simulated using the patient-specific computational heart model. CRT is simulated on the patient-specific computational heart model by adding stimulus currents at specific locations of the anatomical model. The stimulus current is added as additional term in Equation 1. The duration and frequency of the stimulus current can be set to reproduce manufacturers lead programming. Stimulation intervals between pacing leads can also be specified by the user. As a result of the new pacing condition, the heart model will predict new bi-ventricular electrophysiology, dynamics and pressure, which can be used as surrogate predictors of CRT response. Accordingly, it is possible to simulate stimulus current being added at different lead locations, as well as different durations and frequency of stimulus current. Based on the output simulations results, it can be determined if a patient will response to CRT and where the leads should be located to achieve the best patient response. The simulation is run using simulation framework described above, with the parameters of the computational heart model set to the stored patient-specific parameters. For example, simulation framework of FIG. 17, in which the master solver 1700 sequentially calls the subs-solvers 1710, 1720, 1730, and 1740, at each time step, can be used to perform the simulation.

Figure 18:
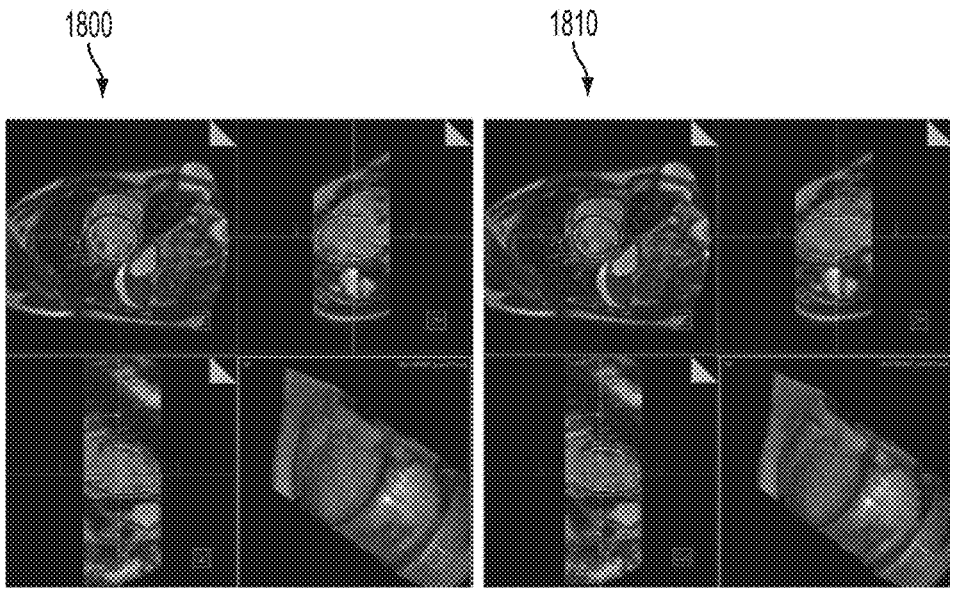
FIGS. 18-25 illustrate exemplary results of patient-specific heart simulation.

FIGS. 18-25 illustrate exemplary results of patient-specific heart simulation using the above described methods. In this example, a stack of short axis MR images was used to detect the LV and RV mesh models in a patient with dilated cardiomyopathy (DCM). FIG. 18 illustrates the LV and RV mesh model detection results for the end-dyastolic and end-systolic frames. As illustrated in FIG. 18, frames 1800 show the LV and RV detection results in end-dyastolic frames, and frames show the LV and RV detection results in end-systolic frames.

Figure 19:
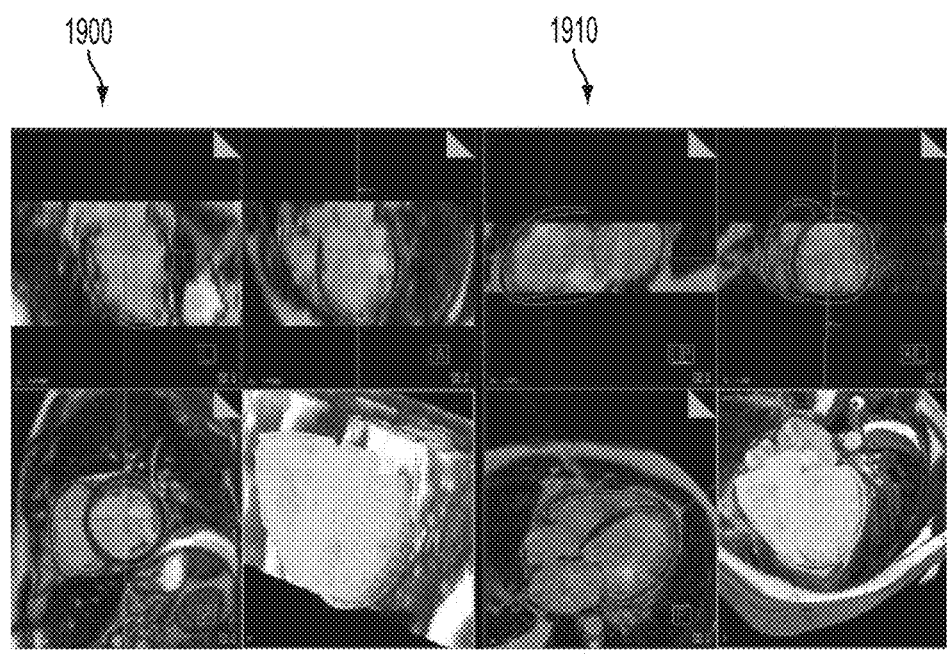

Next the meshes were fused and the resulting mesh was verified using the long axis MR stack. It can be noted, that it is also possible to process both stacks to derive the anatomical model. FIG. 19 illustrates the fused bi-ventricular mesh. As illustrated in FIG. 19, frames 1900 show the fused bi-ventricular mesh in the short-axis stack, and frames 1910 show the fused bi-ventricular mesh in the long axis stack.

Figure 20:
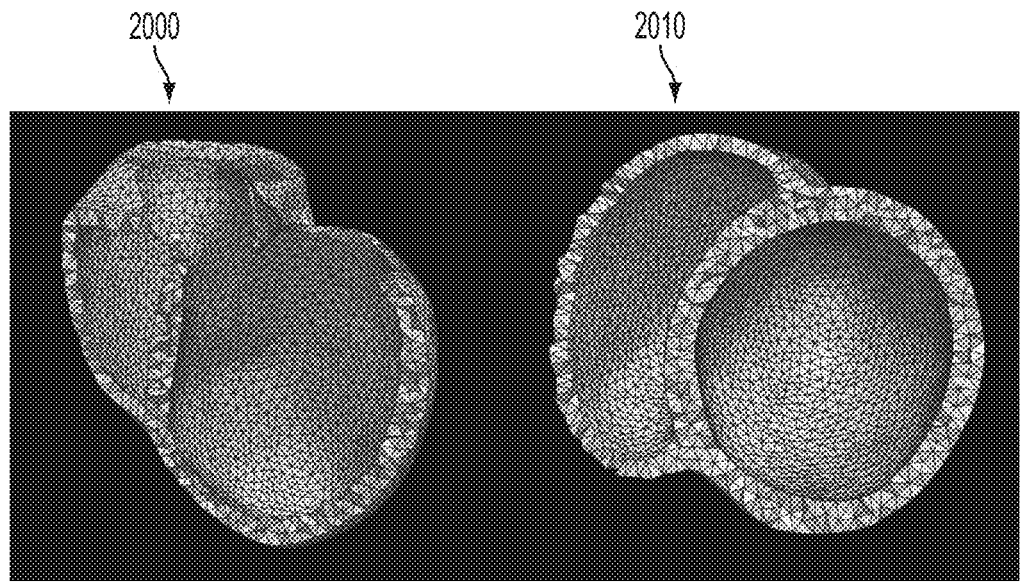
Figure 21:
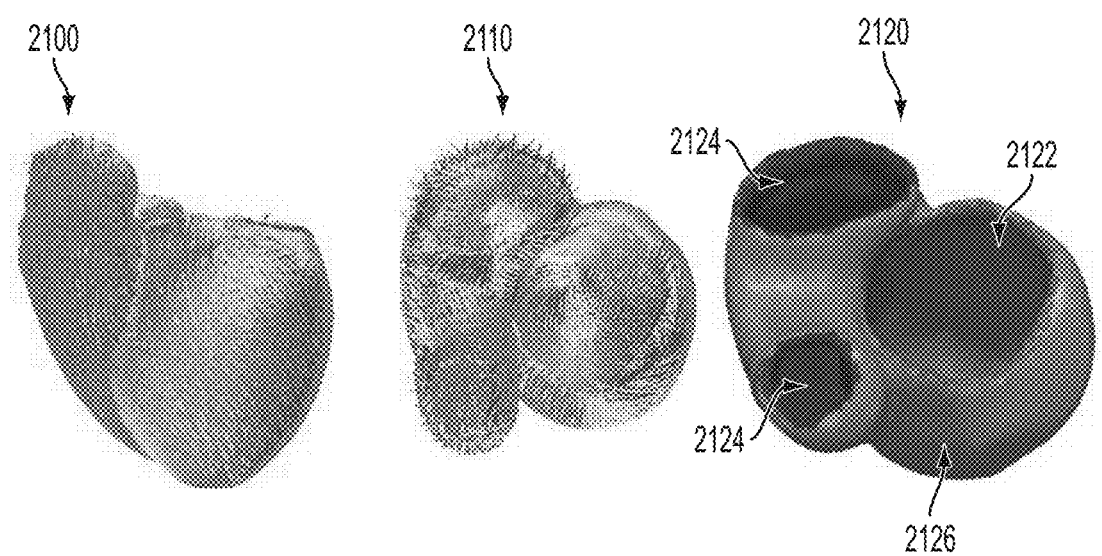

The fused mesh is then transformed into a tetrahedral representation. FIG. 20 shows two views 2000 and 2010 of the tetrahedral representation of the fused left and right ventricles. Once the volumetric, tetrahedral model of the patient's ventricles is built, a synthetic model of the heart fibers is constructed and the surface triangles are automatically tagged to identify the left endocardium, right endocardium and epicardium. FIG. 21 illustrates exemplary results for generating the synthetic fiber model and tagging the tetrahedral mesh. As illustrated in FIG. 21, images 2100 and 2110 show the model of the myocardium fiber orientation mapped on the patient-specific anatomical model. The fibers progressively rotate across the myocardium from −60° on the LV epicardium to +600 on the LV endocardium, and from −80° to +800 for the RV. Image 2120 shows that the outer surface of the tetrahedral mesh is automatically tagged to identify the LV endocardium 2122, RV endocardium 2124, and epicardium 2126.

Figure 22:
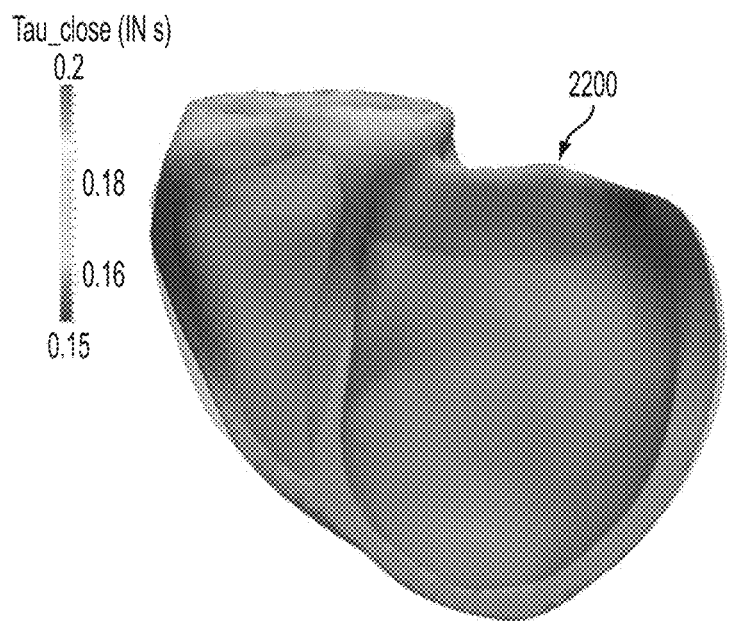

A map of $\tau_{close}$ values is computed on the volumetric mesh to model the heterogeneity of action potential duration (APD) observed in human hearts, as $\tau_{close}$ has a direct influence on the simulated action potential duration in our model. The purpose is to model the longer APD of the septal myocytes compared to free wall. FIG. 22 illustrates the map of $\tau_{close}$ values 2200 on the patient-specific anatomical model.

Figure 23:
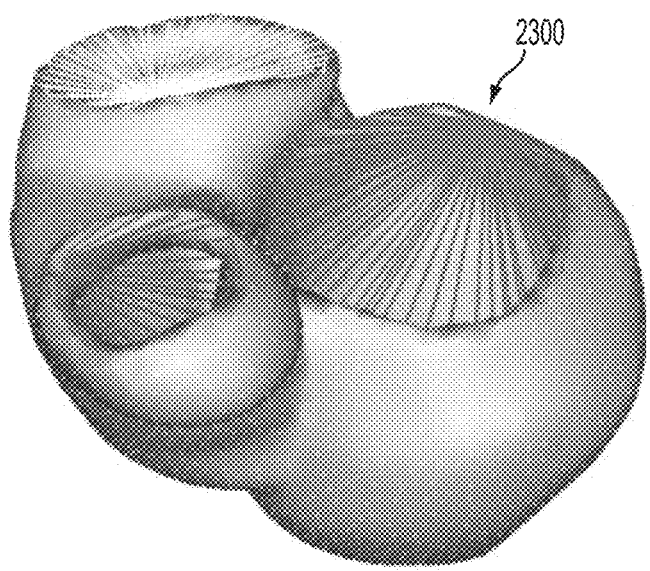

Cardiac electro-mechanics were simulated based on the generated patient-specific anatomical model. The system automatically recognizes the chamber boundaries for volume and pressure computation. FIG. 23 illustrates exemplary automatic detection results 2300 of the chamber boundaries for volume and pressure computation. The strength of the active force, $\sigma_0$, is adjusted by considering the dynamic cine MRI such that the simulated ejection fraction matches the measured one. Cardiac electrophysiology is triggered over the entire endocardium surface as an approximation of the fast conductivity in the Purkinje fibers. The potential then diffuses across the myocardium at a conduction velocity of 500 mm·s$^{-1}$. Cardiac electrophysiology, tissue stiffness and boundary conditions are not adjusted in this exemplary experiment.

Figure 24:
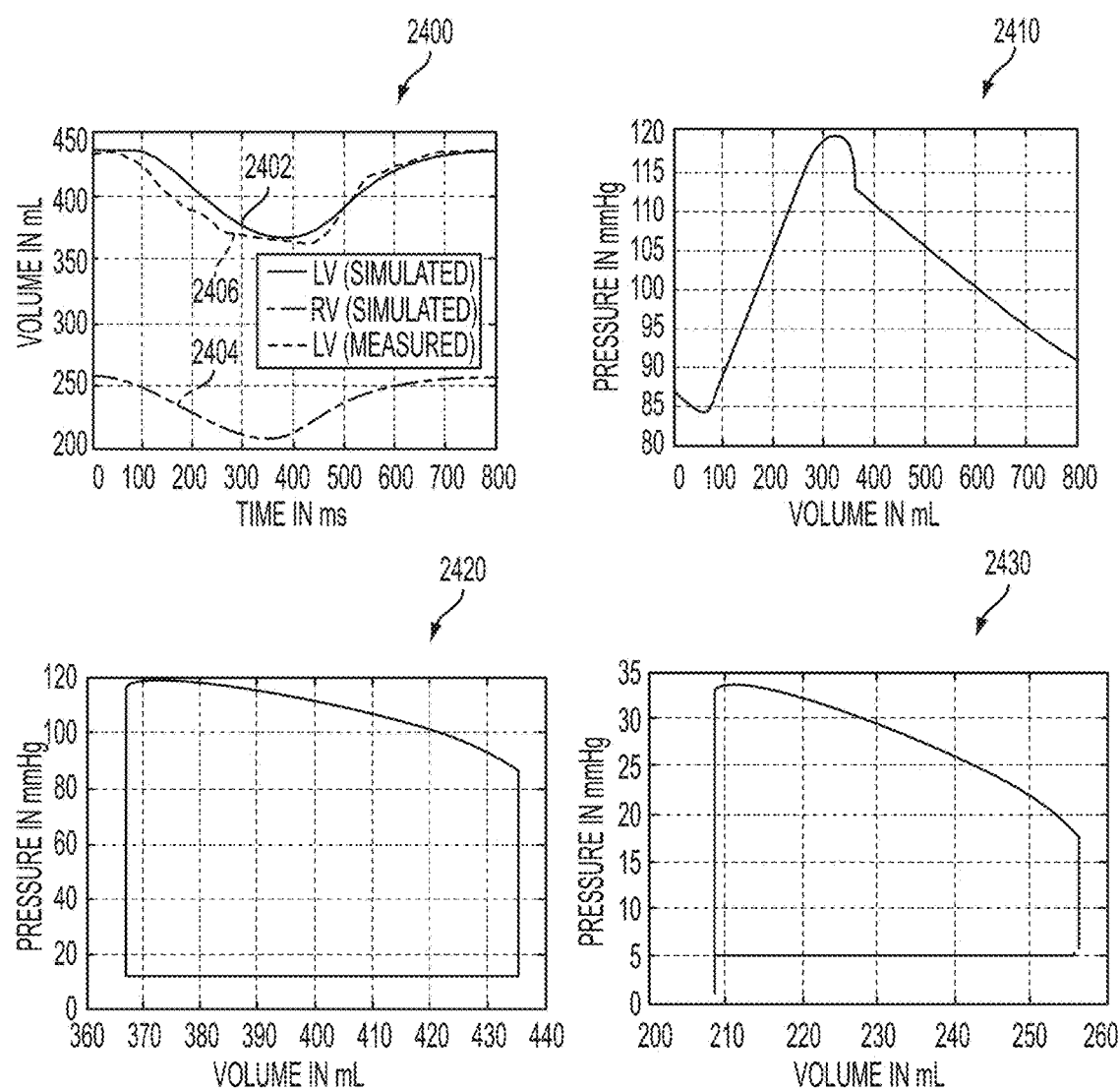

FIG. 24 illustrates exemplary simulated volume curves and pressure-volume loops. It should be observed that all values are computed from the models. As shown in FIG. 24, image 2400 shows simulated volume curves for the LV 2402 and the RV 2404, as well as a measured volume curve for the LV 2406. BY adjusting the active contraction force, the simulated LV volume curve 2402 accurately capture the LV volume variation measured from the images. Image 2410 shows the aortic pressure, which was modeled using a Windkessel model based on the output blood flow. Images 2420 and 2430 show pressure-volume loops for the LV and RV, respectively, each of which illustrates the four different cardiac phases.

Figure 25:
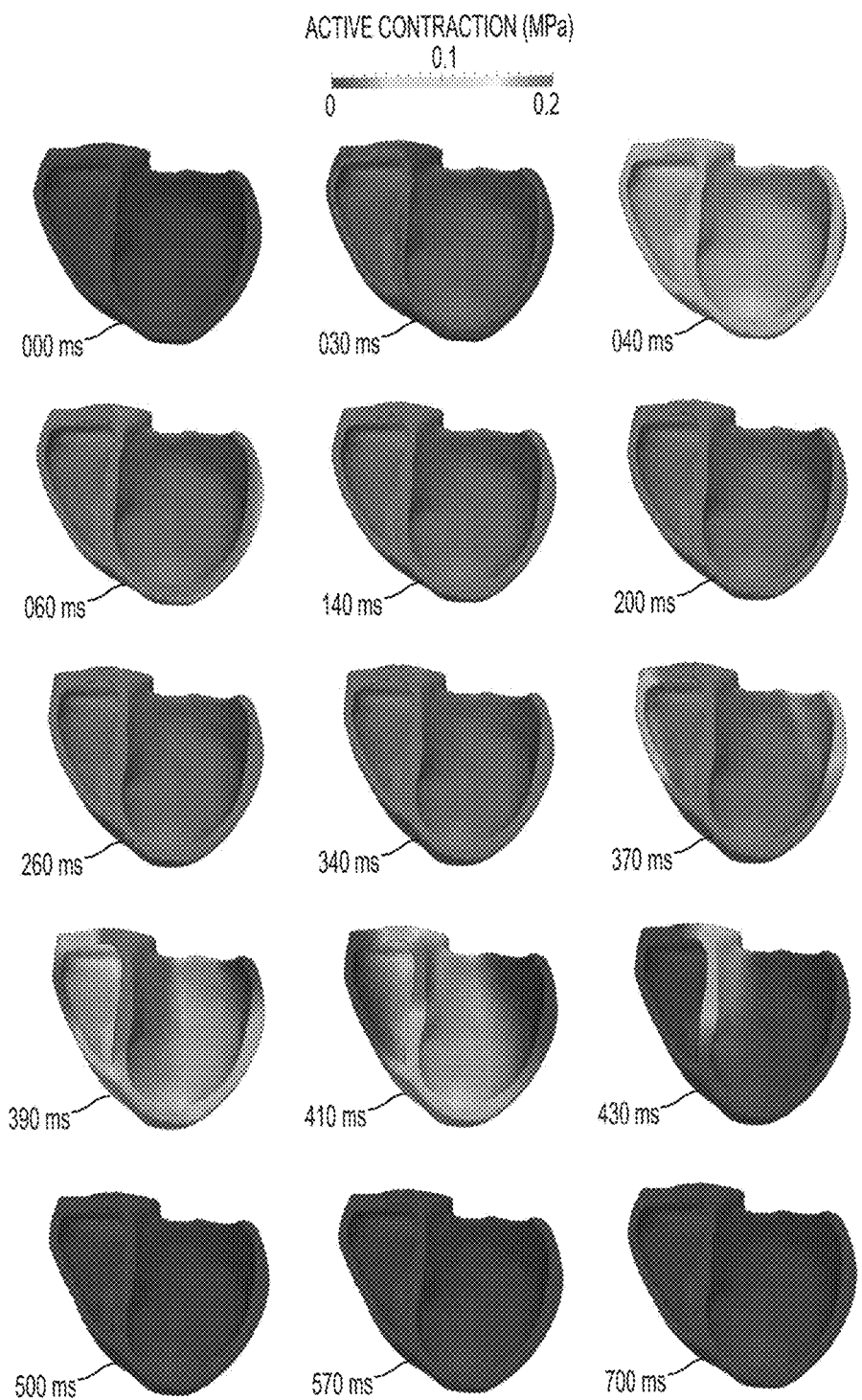

FIG. 25 illustrates a sequence of frames illustrating the second simulated heart beat in the patient. The shading in FIG. 25 represents the active contraction in the heart tissue. As can be seen in FIG. 25, the simulation has been able to reproduce the cardiac function in that patient, in particular ejection fraction and ventricular volume changes. For this first experiment, atrial pressure is constant.

Figure 26:
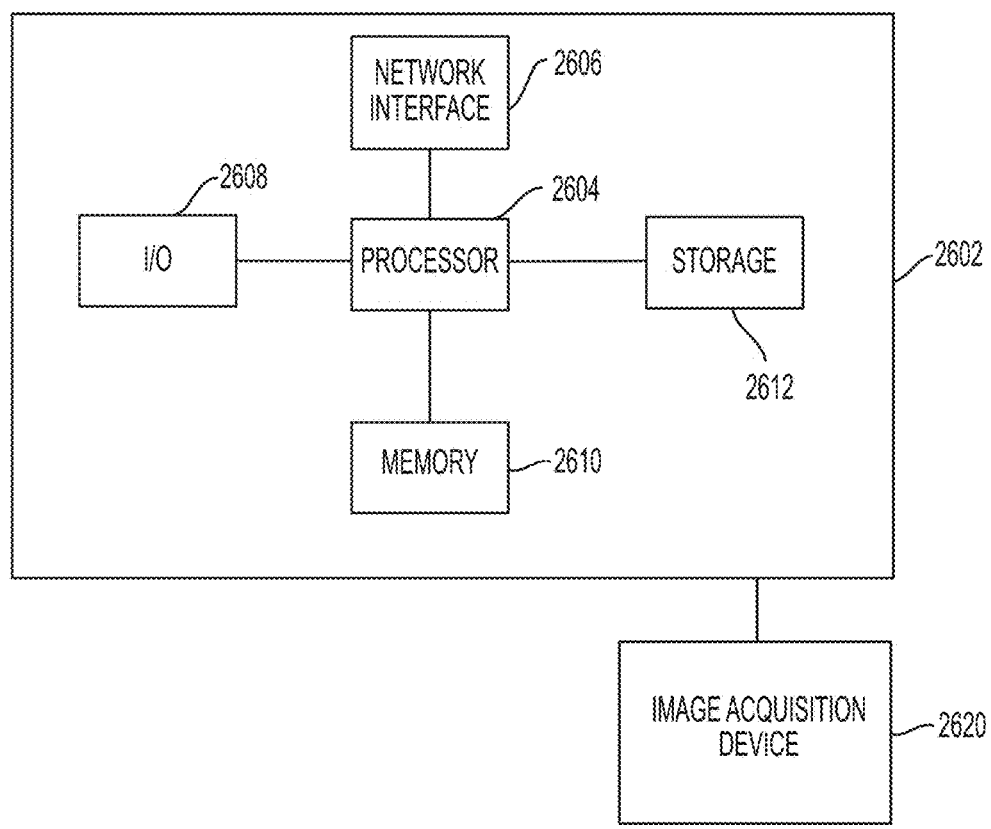
FIG. 26 is a high-level block diagram of a computer capable of implementing the present invention.

The above-described methods for generating a patient-specific anatomic model of the heart, generating a patient-specific computational model of the heart, and performing patient-specific CRT simulations can be implemented on a computer using well-known computer processors, memory units, storage devices, computer software, and other components. A high-level block diagram of such a computer is illustrated in FIG. 26. Computer 2602 contains a processor 2604, which controls the overall operation of the computer 2602 by executing computer program instructions which define such operation. The computer program instructions may be stored in a storage device 2612 (e.g., magnetic disk) and loaded into memory 2610 when execution of the computer program instructions is desired. Thus, the steps of the methods of FIGS. 1, 2, 3, 4, 16 and 17 may be defined by the computer program instructions stored in the memory 2610 and/or storage 2612 and controlled by the processor 2604 executing the computer program instructions. An image acquisition device 2620, such as an MR scanning device, Ultrasound device, etc., can be connected to the computer 2602 to input image data to the computer 2602. It is possible to implement the image acquisition device 2620 and the computer 2602 as one device. It is also possible that the image acquisition device 2620 and the computer 2602 communicate wirelessly through a network. The computer 2602 also includes one or more network interfaces 2606 for communicating with other devices via a network. The computer 2602 also includes other input/output devices 2608 that enable user interaction with the computer 2602 (e.g., display, keyboard, mouse, speakers, buttons, etc.). Such input/output devices 2608 may be used in conjunction with a set of computer programs as an annotation tool to annotate volumes received from the image acquisition device 2620. One skilled in the art will recognize that an implementation of an actual computer could contain other components as well, and that FIG. 26 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:
1. A method for patient-specific cardiac therapy planning, comprising:
generating a patient-specific anatomical model of left and right ventricles from medical image data of a patient;
generating a patient-specific computational heart model based on the patient-specific anatomical model of the left and right ventricles and patient-specific clinical data, wherein generating a patient-specific computational heart model based on the patient-specific anatomical model of the left and right ventricles and patient-specific clinical data comprises:
determining patient-specific parameters of the computational heart model based on the patient-specific anatomical model of the left and right ventricles and the patient-specific clinical data by:
simulating heart function using the computational heart model, and
adjusting parameters of the computational heart model to control simulated clinical parameters resulting from the simulation of heart function using the computational heart model to match corresponding measured clinical parameters for the patient; and simulating cardiac resynchronization therapy (CRT) at one or more anatomical locations using the patient-specific computational heart model by, wherein the computational heart model includes a cardiac electrophysiology module that simulates cardiac electrophysiology, a cardiac biomechanical module, and a cardiac boundary conditions module and the step of simulating CRT at one or more anatomical locations using the patient-specific computational heart model comprises:

simulating heart function with the patient-specific computational heart model with a stimulated current introduced at the one or more anatomical locations in the cardiac electrophysiological module of the computational heart model.

2. The method of claim 1, wherein the step of generating a patient-specific anatomical model of left and right ventricles from medical image data of a patient comprises:

detecting a patient-specific left ventricle model and a patient-specific right ventricle model in the medical image data; and fusing the left ventricle model and the right ventricle model into a single bi-ventricular volumetric mesh.

3. The method of claim 2, wherein the step of generating a patient-specific anatomical model of left and right ventricles from medical image data of a patient further comprises:

mapping spatial information corresponding to at least one of scars, grey zones, or fibrosis onto a tetrahedral representation of bi-ventricular volumetric mesh.

4. The method of claim 2, wherein the step of generating a patient-specific anatomical model of left and right ventricles from medical image data of a patient further comprises:

generating a model of fiber orientation based on the bi-ventricular volumetric mesh.

5. The method of claim 4, wherein the step of generating a model of fiber orientation based on the bi-ventricular volumetric mesh comprises:

determining a constant orientation for fibers on the epicardium and endocardium between a base plane and an apex of the heart;

determining fibers around the mitral, tricuspid, and pulmonary valves to have a circumferential orientation and fibers around the left ventricle outflow tract to have a longitudinal orientation;

performing geodesic interpolation of fiber orientations for fibers on the endocardium and epicardium between the base plane and the valves; and calculating orientations of fibers across the myocardium using linear interpolation.

6. The method of claim 1, wherein the electrophysiological module comprises a phenomenological model that models the change in trans-membrane potential as a summation of inward current, outward current, stimulated current, and a diffusion term.

7. The method of claim 6, wherein the electrophysiological module comprises a first phenomenological model to model trans-membrane potential in the Purkinje fibers coupled with a second phenomenological model to model trans-membrane potential in the myocardium.

8. The method of claim 1, wherein the step of adjusting the parameters of the computational heart model to control simulated clinical parameters resulting from the simulation of heart function using the computational heart model to match corresponding measure clinical parameters for the patient comprises:

adjusting a tissue diffusivity parameter of the electrophysiological module to align a simulated QRS with a QRS of the patient measured using ECG.

9. The method of claim 1, wherein the cardiac biomechanical module comprises a passive component that models an elasticity of the myocardium tissue and an active component that models the active contraction of the muscle in response to an action potential.

10. The method of claim 9, wherein the passive component comprises a co-rotational elasticity model.

11. The method of claim 9, wherein the passive component comprises a hyper-elastic model.

12. The method of claim 9, wherein the active component comprises a multi-scale model of myocyte contraction.

13. The method of claim 9, wherein the step of adjusting the parameters of the computational heart model to control simulated clinical parameters resulting from the simulation of heart function using the computational heart model to match corresponding measure clinical parameters for the patient comprises:

adjusting a tissue stiffness parameter of the passive component of the cardiac biomechanical module to minimize differences between simulated cardiac motion and observed cardiac motion in the medical image data; and adjusting an active contraction strength parameter of the active component of the cardiac biomechanical module to minimize differences between simulated cardiac motion and observed cardiac motion in the medical image data and to minimize differences between a simulated ejection fraction and a measured ejection fraction for the patient.

14. The method of claim 1, wherein the cardiac boundary conditions module models hemodynamics parameters using lumped parameters within each of the left ventricle and the right ventricle, models arterial pressure using a lumped Windkessel model, models atrial pressure using a lumped model, and models the cardiac phases as sequential states.

15. The method of claim 14, wherein the cardiac boundary conditions module models ventricular pressure in isovolumetric phases using correction and prediction model that corrects a current pressure estimate at a current time step such that endocardial volume is preserved and predicts a next pressure estimate at the next time step.

16. The method of claim 14, wherein the cardiac boundary conditions module models an effect of arteries and atria on ventricular motion using a base stiffness model.

17. The method of claim 14, wherein the cardiac boundary conditions module models effects of neighboring organs and the pericardium on ventricular motion using a pericardium constraint model.

18. The method of claim 1, wherein the simulation of the CRT using the patient-specific heart model calculates changes in cardiac parameters after the simulated CRT, and changed cardiac parameters are used as predictors for therapy planning.

19. An apparatus for patient-specific cardiac therapy planning, comprising:

a processor; and a memory storing computer program instructions, which when executed by the processor cause the process to perform operations comprising:

generating a patient-specific anatomical model of left and right ventricles from medical image data of a patient;

generating a patient-specific computational heart model based on the patient-specific anatomical model of the left and right ventricles and patient-specific clinical data, wherein generating a patient-specific computational heart model based on the patient-specific anatomical model of the left and right ventricles and patient-specific clinical data comprises:

determining patient-specific parameters of the computational heart model based on the patient-specific anatomical model of the left and right ventricles and the patient-specific clinical data by:

simulating heart function using the computational heart model, and adjusting parameters of the computational heart model to control simulated clinical parameters resulting from the simulation of heart function using the computational heart model to match corresponding measured clinical parameters for the patient; and simulating CRT at one or more anatomical locations using the patient-specific computational heart model, wherein the computational heart model includes a cardiac electrophysiology module that simulates cardiac electrophysiology, a cardiac biomechanical module, and a cardiac boundary conditions module and simulating CRT at one or more anatomical locations using the patient-specific computational heart model comprises:

simulating heart function with the patient-specific computational heart model with a stimulated current introduced at the one or more anatomical locations in the cardiac electrophysiological module of the computational heart model.

20. The apparatus of claim 19, wherein generating a patient-specific anatomical model of left and right ventricles from medical image data of a patient comprises:

detecting a patient-specific left ventricle model and a patient-specific right ventricle model in the medical image data; and fusing the left ventricle model and the right ventricle model into a single bi-ventricular volumetric mesh.

21. The apparatus of claim 20, wherein generating a patient-specific anatomical model of left and right ventricles from medical image data of a patient further comprises:

generating a model of fiber orientation based on the bi-ventricular volumetric mesh.

22. A non-transitory computer readable medium storing computer program instructions for patient-specific cardiac therapy planning, the computer program instructions when executed by a processor causing the processor to perform operations comprising:

generating a patient-specific anatomical model of left and right ventricles from medical image data of a patient;

generating a patient-specific computational heart model based on the patient-specific anatomical model of the left and right ventricles and patient-specific clinical data, wherein generating a patient-specific computational heart model based on the patient-specific anatomical model of the left and right ventricles and patient-specific clinical data comprises:

determining patient-specific parameters of the computational heart model based on the patient-specific anatomical model of the left and right ventricles and the patient-specific clinical data by:

simulating heart function using the computational heart model, and adjusting parameters of the computational heart model to control simulated clinical parameters resulting from the simulation of heart function using the computational heart model to match corresponding measured clinical parameters for the patient; and simulating cardiac resynchronization therapy (CRT) at one or more anatomical locations using the patient-specific computational heart model, wherein the computational heart model includes a cardiac electrophysiology module that simulates cardiac electrophysiology, a cardiac biomechanical module, and a cardiac boundary conditions module and the simulating CRT at one or more anatomical locations using the patient-specific computational heart model comprises:

simulating heart function with the patient-specific computational heart model with a stimulated current introduced at the one or more anatomical locations in the cardiac electrophysiological module of the computational heart model.

23. The non-transitory computer readable medium of claim 22, wherein the operation of generating a patient-specific anatomical model of left and right ventricles from medical image data of a patient comprises:

detecting a patient-specific left ventricle model and a patient-specific right ventricle model in the medical image data; and fusing the left ventricle model and the right ventricle model into a single bi-ventricular volumetric mesh.

24. The non-transitory computer readable medium of claim 23, wherein the operation of generating a patient-specific anatomical model of left and right ventricles from medical image data of a patient further comprises:

generating a model of fiber orientation based on the bi-ventricular volumetric mesh.

\* \* \* \* \*